United States Patent
Ito et al.

(10) Patent No.: US 8,778,975 B2
(45) Date of Patent: Jul. 15, 2014

(54) HELICOBACTER PYLORI ERADICATING AGENT HAVING INHIBITORY ACTIVITY ON GASTRIC ACID SECRETION

(75) Inventors: Masaharu Ito, Tokyo (JP); Masaichi Yamamoto, Tokyo (JP)

(73) Assignee: Link Geonomics, Inc., Tokyo (JP)

( * ) Notice: Subject to any disclaimer, the term of this patent is extended or adjusted under 35 U.S.C. 154(b) by 831 days.

(21) Appl. No.: 12/519,453

(22) PCT Filed: Dec. 18, 2007

(86) PCT No.: PCT/JP2007/001419
§ 371 (c)(1),
(2), (4) Date: Mar. 8, 2010

(87) PCT Pub. No.: WO2008/075462
PCT Pub. Date: Jun. 26, 2008

(65) Prior Publication Data
US 2010/0173944 A1    Jul. 8, 2010

(30) Foreign Application Priority Data
Dec. 18, 2006  (JP) ................................. 2006-340323

(51) Int. Cl.
*A61K 31/4439* (2006.01)
*C07D 401/12* (2006.01)

(52) U.S. Cl.
USPC ....................................... 514/341; 546/273.7

(58) Field of Classification Search
USPC ....................................... 546/273.7; 514/341
See application file for complete search history.

(56) References Cited

U.S. PATENT DOCUMENTS 4,727,150 A * 2/1988 Nohara et al. ............. 546/273.7

FOREIGN PATENT DOCUMENTS

| EP | 0 1 75 464 A1 | 3/1986 |
| EP | 1 411 053 A1 | 4/2004 |
| JP | 61-50979 | 5/1994 |

OTHER PUBLICATIONS

Kuhler et al., J. Med. Chem., 41:1777-1788 (1998).

* cited by examiner

*Primary Examiner* — Patricia L Morris
(74) *Attorney, Agent, or Firm* — Edwards Wildman Palmer LLP; Peter F. Corless

(57) ABSTRACT

Disclosed are: a compound which is stable in an acid, has an antibacterial effect against a bacterium *Helicobacter pylori*, can exert a satisfactory level of an antibacterial effect when used singly, does not affect an enteric bacterium, has an antibacterial effect against a bacterium resistant to an antibacterial agent, and has an inhibitory effect on gastric acid secretion; and a pharmaceutical composition comprising the compound. Specifically disclosed are: a compound represented by the general formula (I) or a salt thereof; and a pharmaceutical composition comprising the compound or the salt thereof:

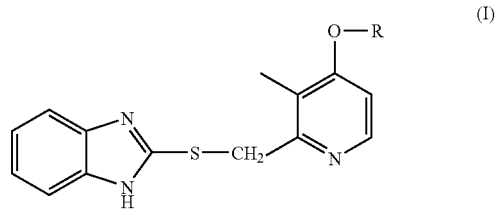

wherein R represents a linear alkyl group having 4 to 8 carbon atoms, preferably 5 to 7 carbon atoms.

3 Claims, 2 Drawing Sheets

HELICOBACTER PYLORI ERADICATING AGENT HAVING INHIBITORY ACTIVITY ON GASTRIC ACID SECRETION

TECHNICAL FIELD

The present invention relates to a *Helicobacter pylori* eradicating agent having also an excellent gastric acid secretion inhibiting action.

BACKGROUND ART

Gastritis, gastric ulcer and duodenal ulcer are diseases which develop as a result of complicated entanglement of factors such as stress, genetic predisposition and lifestyle habit. In recent years, attention is being paid to the bacterium *Helicobacter pylori* (*H. pylori*) as one of the principal causes. Since the success of Warren and Marshall in the isolation and culture of spiral-shaped bacteria from gastric biopsy specimens in 1983, vigorous research has been carried out on the relationship between the subject bacteria and gastritis, gastric ulcer, duodenal ulcer and gastric cancer. As a result, the infection rate of *Helicobacter pylori* (*H. pylori*) is reported to be such that while the positive rate in normal stomach was about 4%, the positive rate was as high as about 83% for chronic gastritis, about 69% for gastric ulcer, about 92% for duodenal ulcer, and about 51% for non-ulcer dyspepsia syndrome (see Non-Patent Document 1). Furthermore, infection by the bacterium *Helicobacter pylori* is strongly correlated to the incidence rate of gastric cancer, and in 1994, the International Agency for Research on Cancer of the WHO declared the bacterium *Helicobacter pylori* as a carcinogen indicating a strong causal relationship.

The mainstream of the treatment for gastritis, gastric ulcer, duodenal ulcer and the like has been represented by symptomatic therapy, in which gastric acid secretion inhibitors which inhibit gastric acid secretion, such as H2 blockers and proton pump inhibitors, and mucosal protective agents are utilized for the purpose of improving subjective symptoms such as epigastric pain, and accelerating the healing of gastric ulcer. However, it is reported that even though the lesions are temporarily healed by these drugs, if the treatment is stopped, about 80% of the patients have a relapse within one year (see Non-Patent Document 1). On the other hand, it is also reported that when *Helicobacter pylori* bacteria are eradicated, the one-year recurrence rate was 10% or less for duodenal ulcer, and the rate was low also for the case of gastric ulcer (see Non-Patent Document 2).

Currently, as a method for eradicating *Helicobacter pylori* bacteria, treatment is carried out, such as by using a proton pump inhibitor (PPI) in combination with antibacterial agents such as amoxicillin and clarithromycin, in large quantities over one week or more, and in some cases, adding metronidazole thereto. However, administration of antibacterial agents in large quantities also causes disinfection of useful bacteria in the intestine, and as a result, there is concern for adverse side effects such as loose stool, diarrhea and taste disturbance, glossitis, stomatitis, abnormality of hepatic function, and hemorrhagic enteritis, as well as the possibility of promoting the emergence of methicillin-resistant *Staphylococcus aureus* (MRSA).

To date, a large number of patent applications have been filed with regard to pyridine derivatives, for the applications as antiulcer agents, gastric acid secretion inhibitors, antibacterial agents against *Helicobacter pylori* bacteria, and the like (see Patent Documents 1 to 8). However, there is not found any compound which combines an anti-*Helicobacter pylori* action and a gastric acid secretion inhibiting action in a well balanced manner, and is capable of eradicating *Helicobacter pylori* bacteria, when used as a sole agent.

Furthermore, a compound having an anti-*Helicobacter pylori* action in vitro and a gastric acid secretion inhibiting action has been discovered (see Non-Patent Document 3). However, in a *Helicobacter pylori*-infected model using Mongolian gerbil, which is considered to reflect human infection by *Helicobacter pylori* bacteria, the effectiveness could not be verified, and development of the agent has been abandoned.

In spite of such extensive efforts as described above, triple therapy is still widely practiced at present, for the eradication of *Helicobacter pylori* bacteria. The reason is that proton pump inhibitors such as omeprazole, lansoprazole and rabeprazole, and clarithromycin are all extremely unstable in acid, and it is difficult with amoxicillin to exhibit antibacterial activity under acidic conditions. That is, there was a need to administer large quantities of the aforementioned acid-labile antibiotic substances, while gastric acid had been strongly inhibited by proton pump inhibitors which were administered as an enteric preparation.

Patent Document 1: JP-A No. 61-50979
Patent Document 2: JP-A No. 3-173817
Patent Document 3: JP-A No. 5-247035
Patent Document 4: JP-A No. 59-181277
Patent Document 5: JP-A No. 7-69888
Patent Document 6: JP-A No. 3-48680
Patent Document 7: JP-A No. 2-209809
Patent Document 8: JP-A No. 58-39622
Non-Patent Document 1: Martin J. Blaser: Clin. Infectious Disease, 15; 386-393, 1992
Non-Patent Document 2: Graham D. Y., et al.: Ann. Intern. Med., 116; 705-708, 1992
Non-Patent Document 3: Thomas C. Kuehler, et al., J. Med. Chem. 1998, 41, 1777-1788

DISCLOSURE OF THE INVENTION

Problems to be Solved by the Invention

The present invention provides a novel pharmaceutical composition for preventing and/or treating diseases involving *Helicobacter pylori* bacteria and/or diseases involving gastric acid secretion, which is effective in the prevention and/or treatment of *Helicobacter pylori* bacteria-associated diseases and also acts specifically against *Helicobacter pylori* bacteria, and which does not exert an action on intestinal bacteria, while being stable against acid and having a gastric acid secretion inhibiting action; and a compound or a salt thereof, which is useful as an active ingredient for the composition.

Means for Solving the Problems

The inventors have conducted a search for a compound which satisfies the following conditions, as a goal:
1) To be stable against acid; 2) to have satisfactory antibacterial action against *Helicobacter pylori* bacteria; 3) to act specifically against *Helicobacter pylori* bacteria, while not exerting an action on intestinal bacteria; 4) to exhibit effects even on those bacteria which show resistance to the antibacterial agents used in the treatment of *Helicobacter pylori* bacteria-associated diseases; 5) to have a gastric acid secretion inhibiting action; and 6) to exhibit a bacteria eradicating effect in an animal model for infection by *Helicobacter pylori* bacteria, when used as a sole agent (Hirayama et al.; J. Gastroenterol., 1996. 31, (Suppl. 9), 24-8).

As a result, the inventors found a family of compounds which are stable in acid, have a strong anti-*Helicobacter pylori* activity with an MIC of 0.1 µg/ml or less, do not have an action on the bacteria indigenous to human being, exhibit an antibacterial action specifically against *Helicobacter pylori* bacteria, exhibit effectiveness even against bacteria resistant to antibiotics such as clarithromycin, which is clinically widely used in the eradication of *Helicobacter pylori* bacteria, and also offer specific operating effects in combination with a gastric acid secretion inhibiting action. The inventors of the present invention also found that the relevant compounds exhibit an eradicating effect in a *Helicobacter pyloric* bacteria-infected animal model when used as individual agents. Based on these findings, the inventors completed the present invention.

Specifically, the present invention relates to a pyridine derivative represented by formula (I) or a pharmacologically acceptable salt thereof:

[Chemical Formula 1]

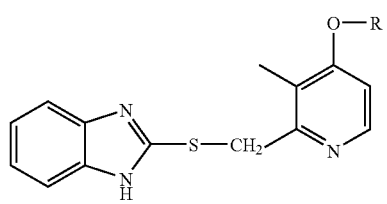

(I)

wherein R represents a linear alkyl group having 4 to 8 carbon atoms.

The present invention also relates to a pharmaceutical composition including the pyridine derivative represented by the above formula (I) or a pharmacologically acceptable salt thereof, and more particularly, to a pharmaceutical composition including a pyridine derivative represented by the above formula (I) or a pharmacologically acceptable salt thereof, and a pharmaceutically acceptable carrier.

Furthermore, the present invention relates to a use of the pyridine derivative represented by the formula (I) or a pharmacologically acceptable salt thereof, for the production of a preparation for preventing or treating a disease involving *Helicobacter pylori* bacteria and/or a disease involving gastric acid secretion.

The present invention also relates to a method for preventing or treating a disease involving *Helicobacter pylori* bacteria and/or a disease involving gastric acid secretion, the method including administering an effective amount of the pyridine derivative represented by the formula (I) or a pharmacologically acceptable salt thereof, to a patient having a disease involving *Helicobacter pylori* bacteria and/or a disease involving gastric acid secretion, or a patient having a risk of contracting the disease.

The present invention also relates to a method for producing the pyridine derivative represented by the formula (I) or a pharmacologically acceptable salt thereof, the method including reacting a compound represented by the following formula (II):

[Chemical Formula 2]

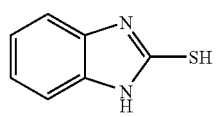

(II)

with a compound represented by the following formula (III):

[Chemical Formula 3]

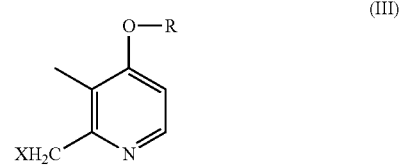

(III)

wherein R represents a linear alkyl group having 4 to 8 carbon atoms; and X represents a halogen atom.

The present invention also relates to a compound represented by the formula (III) described above.

The present invention may be described in more detail, as follows.

(1) A pyridine derivative represented by the formula (I) or a pharmacologically acceptable salt thereof.

(2) The pyridine derivative according to (1) above or a pharmacologically acceptable salt thereof, wherein R in the formula (I) is a linear alkyl group having 5 to 7 carbon atoms.

(3) A pharmaceutical composition including the pyridine derivative according to (1) or (2) above or a pharmacologically acceptable salt thereof, and a pharmaceutically acceptable carrier.

(4) The pharmaceutical composition according to (3) above, wherein the pharmaceutical composition is intended to prevent or treat a disease involving *Helicobacter pylori* bacteria and/or a disease involving gastric acid secretion.

(5) The pharmaceutical composition according to (4) above, wherein the disease is gastritis, gastric ulcer, duodenal ulcer, non-ulcer dyspepsia syndrome, gastric MALT lymphoma, gastric hyperplastic polyp, digestive system cancer or pancreatitis resulting from hypergastrinemia caused by *Helicobacter pylori*, an inflammatory bowel disease caused by *Helicobacter pylori*, or gastric cancer after endoscopic resection of early gastric cancer.

(6) The pharmaceutical composition according to any one of (3) to (5) above, further including another gastric acid secretion inhibitor and/or an antibacterial agent as an active ingredient.

(7) Use of the pyridine derivative according to (1) or (2) above or a pharmacologically acceptable salt thereof, for the production of a preparation for preventing or treating a disease involving *Helicobacter pylori* bacteria and/or a disease involving gastric acid secretion.

(8) The use according to (7) above, wherein the disease is gastritis, gastric ulcer, duodenal ulcer, non-ulcer dyspepsia syndrome, gastric MALT lymphoma, gastric hyperplastic polyp, digestive system cancer or pancreatitis resulting from hypergastrinemia caused by *Helicobacter pylori*, an inflammatory bowel disease caused by *Helicobacter pylori*, or gastric cancer after endoscopic resection of early gastric cancer.

(9) The use according to (7) or (8) above, wherein the preparation for preventing or treating a disease involving *Helicobacter pylori* bacteria and/or a disease involving gastric acid secretion further includes another gastric acid secretion inhibitor and/or an antibacterial agent as an active ingredient.

(10) A method for preventing or treating a disease involving *Helicobacter pylori* bacteria and/or a disease involving gastric acid secretion, the method including administering an effective amount of the pyridine derivative according to (1) or (2) above or a pharmacologically acceptable salt thereof, to a patient having a disease involving *Helicobacter pylori* bacteria and/or a disease involving gastric acid secretion or having a risk of contracting the disease.

(11) The method according to (10) above, wherein the disease is gastritis, gastric ulcer, duodenal ulcer, non-ulcer dyspepsia syndrome, gastric MALT lymphoma, gastric hyperplastic polyp, digestive system cancer or pancreatitis resulting from hypergastrinemia caused by *Helicobacter pylori*, an inflammatory bowel disease caused by *Helicobacter pylori*, or gastric cancer after endoscopic resection of early gastric cancer.

(12) The method according to (10) or (11) above, wherein administering an effective amount of the pyridine derivative according to (1) or (2) above or a pharmacologically acceptable salt thereof, and concurrently further administering another gastric acid secretion inhibitor and/or an antibacterial agent as a further active agent.

(13) A method for producing the pyridine derivative represented by the formula (I) or a pharmacologically acceptable salt thereof, the method including reacting a compound represented by the above-described formula (II) with a compound represented by the above-described formula (III).

(14) A pharmaceutical composition including the pyridine derivative according to (1) or (2) above or a pharmacologically acceptable salt thereof.

(15) The pharmaceutical composition according to (14) above, intended for the eradication or bacteriostasis of *Helicobacter pylori*, and the inhibition of gastric acid secretion.

(16) The pharmaceutical composition according to (14) or (15) above, including only the pyridine derivative according to (1) or (2) above or a pharmacologically acceptable salt thereof, as an active ingredient.

(17) The pharmaceutical composition according to any one of (14) to (16) above, further including another gastric acid secretion inhibitor and/or an antibacterial agent as an active ingredient.

(18) An anti-*Helicobacter pylori* agent including the pyridine derivative according to (1) or (2) above or a pharmacologically acceptable salt thereof.

(19) A gastric acid secretion inhibitor including the pyridine derivative according to (1) or (2) above or a pharmacologically acceptable salt thereof.

(20) A prophylactic or therapeutic agent for a disease or condition involving *Helicobacter pylori* and/or gastric acid secretion, including the pyridine derivative according to (1) or (2) above or a pharmacologically acceptable salt thereof.

(21) The prophylactic or therapeutic agent according to (20) above, wherein the disease or condition is gastritis, gastric ulcer, duodenal ulcer, non-ulcer dyspepsia syndrome, gastric MALT lymphoma, gastric hyperplastic polyp, or gastric cancer after endoscopic resection of early gastric cancer.

(22) A prophylactic or therapeutic agent for a disease or condition involving *Helicobacter pylori*, including the novel pyridine derivative according to (1) or (2) above or a pharmacologically acceptable salt thereof.

(23) The prophylactic or therapeutic agent according to (21) or (22), wherein the disease or condition is digestive system cancer or pancreatitis resulting from hypergastrinemia caused by *Helicobacter pylori*, or an inflammatory bowel disease caused by *Helicobacter pylori*.

Effects of the Invention

The pyridine derivative or a salt thereof of the present invention not only has an excellent anti-*Helicobacter pylori* bacteria action, but also is extremely stable in acid so that the compound is not decomposed even in the presence of gastric acid and exhibit effectiveness. Furthermore, the compound also has a gastric acid secretion inhibiting action, has a specific eradicating action against *Helicobacter pylori* bacteria when used as a sole agent, and is useful as a prophylactic and/or therapeutic drug for various diseases involving *Helicobacter pylori* bacteria or various diseases associated with excess gastric acid secretion, for example, gastritis, gastric ulcer, duodenal ulcer, non-ulcer dyspepsia syndrome, gastric MALT lymphoma, gastric hyperplastic polyp, gastric cancer after endoscopic resection of early gastric cancer, digestive system cancer or pancreatitis resulting from hypergastrinemia caused by *Helicobacter pylori*, inflammatory bowel diseases caused by *Helicobacter pylori*, or the like.

The pyridine derivative and salts thereof of the present invention are characterized in that the compounds can be used as prophylactic and/or therapeutic drugs effective for these diseases, particularly when used as a sole agent.

BEST MODE FOR CARRYING OUT THE INVENTION

Figure 1:
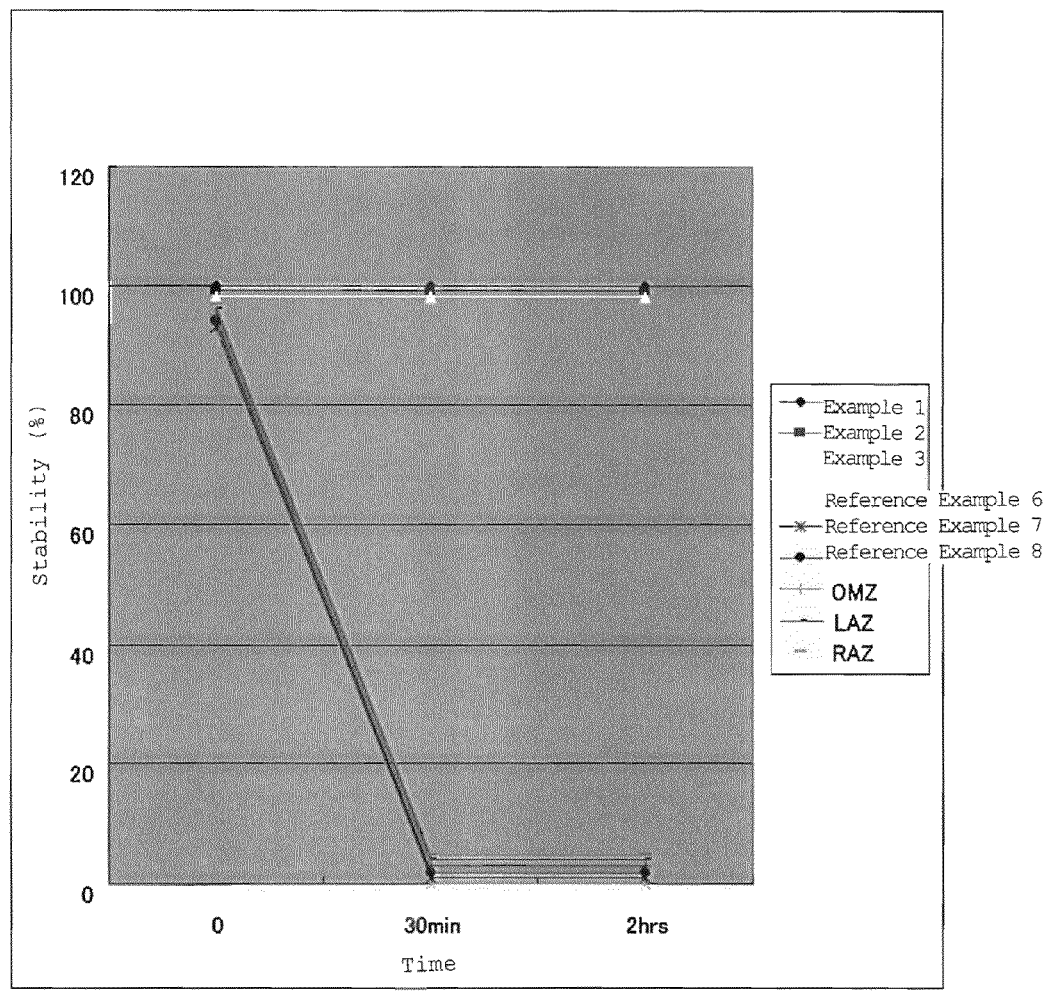
FIG. 1 is a graph showing the results of a stability test for a compound of the present invention and a compound of Comparative Example in an acidic hydrochloric acid solution (pH 2). The vertical axis of FIG. 1 represents stability (residual ratio) (%), while the horizontal axis represents time elapsed (minutes).

The inventors of the present invention have conducted an investigation in detail on 2-(4-alkoxy-3-methylpyridin-2-yl-methylthio)benzimidazole compounds and sulfinyl derivatives thereof, and obtained the following findings. It was found that there are offered highly remarkable operating effects such as that: (1) In a sulfinyl derivative, the activity against *Helicobacter pylori* bacteria has an MIC of 3.0 μg/mL, and although the derivative shows the activity to a certain extent, the derivative is extremely unstable against acid (see Table 1 and FIG. 1); (2) when the number of carbon atoms in the alkoxy group is 4 to 8, and preferably from 5 to 7, the activity against *Helicobacter pylori* bacteria is remarkably excellent, and the MIC is reduced to ⅓ to ¹/₁₀ (see Table 2 and FIG. 2); (3) in the case where the carbon atom at the α-position of the alkoxy group is forming a branched chain, that is, in the case where the alkoxy group is an isoalkoxy group, the activity against *Helicobacter pylori* bacteria is extremely lowered (see Table 3 and Table 6); (4) the compound of the present invention exhibits a potent antibacterial activity against clarithromycin-resistant strains and amoxicillin-insensitive strains (see Table 4); (5) the compound of the present invention is not recognized to have an antibacterial action against various Gram-negative bacteria and Gram-positive bacteria (see Table 5); and (6) the compound of the present invention exhibits a gastric acid secretion inhibiting effect (see Table 7).

As the result, the compound of the present invention is equivalent to or better than the triple combination of omeprazole+amoxicillin+clarithromycin, which is widely utilized over the world as a therapy for eradicating *Helicobacter pylori* bacteria, and particularly, the compound of the present invention has an effectiveness equivalent to or better than that of such triple combination therapy, even when used as a sole agent. Furthermore, the invented compound exhibits a specific antibacterial activity against *Helicobacter pylori* bacteria, and exhibits an antibacterial action against the bacteria that are insensitive or resistant to amoxicillin and clarithromycin. Further, the compound has a gastric acid secretion inhibiting action, is also extremely stable against acid so that the compound is not decomposed even in the presence of gastric acid, and offers highly excellent operating effects from clinical aspects. These characteristic operating effects originate from the point that the methylthio moiety is not in the form of a sulfinyl group in an oxidized state, but in the form of thioether, and the point that the alkoxy group at the 4-position of the pyridine ring is a particular alkyl group.

Furthermore, the pyridine derivative represented by the above-described formula (I) or a salt thereof of the present invention is a novel compound which is not disclosed in the literature.

R in the formula (I) of the present invention is a linear alkyl group having 4 to 8, and preferably 5 to 7, carbon atoms. As for the linear alkyl group according to the present invention, an n-alkyl group is preferred, and there may be mentioned an alkyl group which is —CH$_2$—R' (wherein R' represents a linear alkyl group having 3 to 7, and preferably 4 to 6, carbon atoms), and is not branched at the α-position of the alkoxy group. As for preferred alkyl groups, an n-butyl group, an n-pentyl group, an n-hexyl group, an n-heptyl group, an n-octyl group and the like may be mentioned, and as for more preferred alkyl groups, an n-pentyl group, an n-hexyl group, and an n-heptyl group may be mentioned.

More specifically, as preferred compounds according to the present invention, there may be mentioned
2-[(4-n-butyloxy-3-methylpyridin-2-yl)-methylthio]-1H-benzimidazole;
2-[(4-n-pentyloxy-3-methylpyridin-2-yl)-methylthio]-1H-benzimidazole;
2-[(4-n-hexyloxy-3-methylpyridin-2-yl)-methylthio]-1H-benzimidazole;
2-[(4-n-heptyloxy-3-methylpyridin-2-yl)-methylthio]-1H-benzimidazole; and
2-[(4-n-octyloxy-3-methylpyridin-2-yl)-methylthio]-1H-benzimidazole.

Furthermore, as more preferred compounds of the present invention, there may be mentioned
2-[(4-n-pentyloxy-3-methylpyridin-2-yl)-methylthio]-1H-benzimidazole;
2-[(4-n-hexyloxy-3-methylpyridin-2-yl)-methylthio]-1H-benzimidazole; and
2-[(4-n-heptyloxy-3-methylpyridin-2-yl)-methylthio]-1H-benzimidazole.

The pyridine derivative represented by the formula (I) or a salt thereof of the present invention can be produced by reacting, as raw material compounds, a mercapto derivative represented by the above-described formula (II) with a pyridyl derivative represented by the above-described formula (III). In the pyridyl derivative represented by the formula (III), X is not particularly limited as long as it is a leaving group, but as a preferred leaving group, there may be mentioned a halogen atom. As for the halogen atom, chlorine, bromine, iodine and the like may be mentioned.

The compound represented by the formula (III) is a novel compound, and is useful as an intermediate for the production of the formula (I) of the present invention. The present invention is to provide a compound represented by such formula (III).

This reaction is performed preferably in the presence of a base. As the base used in this reaction, there may be mentioned, for example, alkali metal hydrides such as sodium hydride and potassium hydride; sodium alcoholates such as sodium methoxide and sodium ethoxide; carbonates of alkali metals such as potassium carbonate and sodium carbonate; organic amines such as triethylamine; and the like. Furthermore, as the solvent used in the reaction, there may be mentioned, for example, alcohols such as methanol and ethanol, dimethylsulfoxide and the like. The amount of the base used in the reaction is usually an amount slightly excess compared to an equivalent amount, but a large excess of base may also be used. For example, the amount is about 2 to 10 equivalents, and more preferably about 2 to 4 equivalents. The reaction temperature is usually from 0° C. to near the boiling point of the solvent used, and more preferably, a temperature of about 20° C. to 80° C. may be mentioned. The reaction time can be appropriately selected, but the time is usually, for example, about 0.2 to 24 hours, and more preferably about 0.5 to 2 hours.

The target compound (I) produced by the above-described reaction can be isolated and purified by conventional means such as recrystallization and chromatography.

The pyridine derivative represented by the formula (I) of the present invention can be made into a pharmaceutically acceptable salt by a conventionally used means. Examples of such a salt includes hydrochloride, hydrobromide, hydroiodide, phosphate, nitrate, sulfate, acetate, citrate, and the like.

The raw material compound represented by formula (III), which is used in the production of the pyridine derivative represented by the formula (I) of the present invention, can be produced by the reaction process shown in the following.

Production Method 1

[Chemical Formula 4]

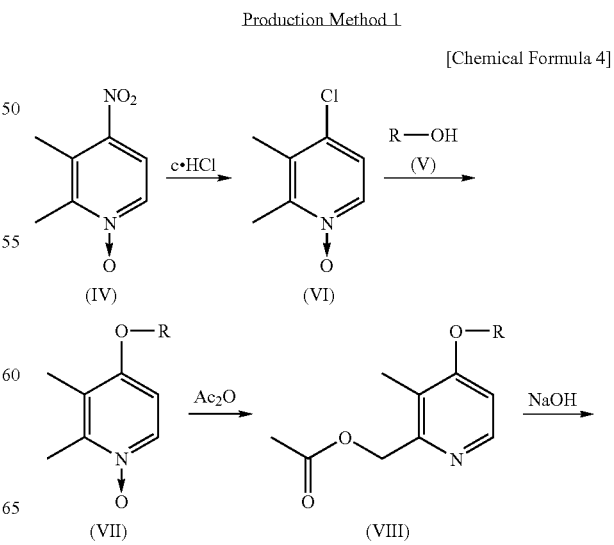

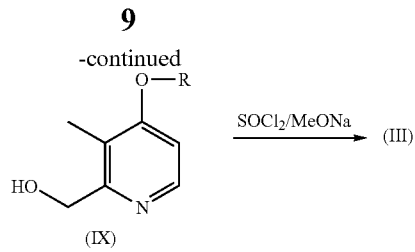

First, a nitro compound represented by formula (IV) is reacted with concentrated hydrochloric acid to produce a chlor derivative (VI), and when this chlor derivative (VI) is reacted with an alcohol derivative ROH (V) in the presence of a base, an alkoxy derivative represented by formula (VII) can be obtained. As the base used in this case, for example, alkali metals such as lithium, sodium and potassium; alkali metal hydrides such as sodium hydride and potassium hydride; alcoholates such as t-butoxypotassium, propoxysodium, ethoxysodium and methoxysodium; carbonates or hydrogen carbonates of alkali metals such as potassium carbonate, lithium carbonate, sodium carbonate, potassium hydrogen carbonate and sodium hydrogen carbonate; alkali metal hydroxides such as sodium hydroxide and potassium hydroxide; and the like may be mentioned. As the solvent used in the reaction, there may be mentioned lower alcohols represented by ROH, as well as ethers such as tetrahydrofuran and dioxane; ketones such as acetone and methyl ethyl ketone; acetonitrile, dimethylformamide, dimethylsulfoxide, and the like. For the reaction temperature, an appropriate temperature from an ice-cold temperature to near the boiling point of the solvent is selected. The reaction time is about 1 to 48 hours.

The alkoxy derivative (VII) thus obtained is heated to about 80 to 120° C. in the presence of acetic anhydride alone, or with a mineral acid such as sulfuric acid or perchloric acid, and thereby a 2-acetoxymethylpyridine derivative represented by formula (VIII) is obtained. The reaction time is usually about 0.1 to 10 hours.

Subsequently, a 2-hydroxymethylpyridine derivative represented by formula (IX) can be produced by subjecting the compound (VIII) to alkali hydrolysis. As for the alkali in this case, there may be mentioned, for example, sodium hydroxide, potassium hydroxide, potassium carbonate, sodium carbonate and the like. As for the solvent used, for example, methanol, ethanol, water and the like may be mentioned. The reaction time is about 0.1 to 2 hours.

Subsequently, by halogenating the compound (IX) with a halogenating agent such as a chlorinating agent like thionyl chloride, a 2-halogenomethylpyridine derivative represented by formula (III) can be produced. As for the solvent used, there may be mentioned, for example, chloroform, dichloromethane, tetrachloroethane and the like. The reaction temperature is usually about 20° C. to 80° C., and the reaction time is about 0.1 to 2 hours.

The compound of the present invention or a salt thereof is stable against acid, and is capable of subjecting *Helicobacter pylori* bacteria to eradication or bacteriostasis even in the body of an animal which belongs to the mammalia (typically, human being). That is, the compound of the present invention or a salt thereof is effective as an anti-*Helicobacter pylori* agent.

The compound of the present invention or a salt thereof can also inhibit gastric acid secretion in an animal which belongs to the mammalia (typically, human being), in addition to the aforementioned action. That is, the compound of the present invention or a salt thereof is also effective as a gastric acid secretion inhibitor.

The present invention also provides a method for subjecting *Helicobacter pylori* to eradication or bacteriostasis in a mammal, and/or a method for inhibiting gastric acid secretion, the method including administering an effective amount of the compound of the present invention or a salt thereof to a mammal in need of the method.

The present invention also provides a use of the compound of the present invention or a salt thereof for the production of an anti-*Helicobacter pylori* agent and/or a gastric acid secretion inhibitor.

The present invention also provides a pharmaceutical composition combining an anti-*Helicobacter pylori* action and a gastric acid secretion inhibiting action, the composition containing the compound of the present invention or a salt thereof as an active ingredient. The compound of the present invention is characterized by providing an anti-*Helicobacter pylori* action and a gastric acid secretion inhibiting action when used as a sole agent. Therefore, it is preferable for the pharmaceutical composition to include the compound of the present invention or a salt thereof only, as the active ingredient. Furthermore, the pharmaceutical composition may further include another gastric acid secretion inhibitor and/or an antibacterial agent as an active ingredient. As the another gastric acid secretion inhibitor, there may be mentioned H2 blockers, proton pump inhibitors and the like. Examples of the H2 blockers that can be used in the present invention include cimetidine, famotidine, ranitidine and the like, while examples of the proton pump inhibitors that can be used in the present invention include lansoprazole, omeprazole, rabeprazole, pantoprazole and the like, but the examples are not limited thereto.

A medicament containing the compound of the present invention or a salt thereof is effective for the prevention or treatment of a disease involving *Helicobacter pylori* and/or gastric acid secretion (preferably, *Helicobacter pylori* and gastric acid secretion). A disease involving *Helicobacter pylori* refers to a disease which is caused or aggravated by the infection, survival or growth of *Helicobacter pylori* in vivo. A disease involving gastric acid secretion refers to a disease which is caused or aggravated by the secretion of gastric acid. Examples of such a disease include gastritis, gastric ulcer, duodenal ulcer, non-ulcer dyspepsia syndrome, gastric MALT lymphoma, gastric hyperplastic polyp, digestive system cancer or pancreatitis resulting from hypergastrinemia caused by *Helicobacter pylori*, inflammatory bowel diseases caused by *Helicobacter pylori*, gastric cancer after endoscopic resection of early gastric cancer, and the like. In regard to the gastric cancer after endoscopic resection of early gastric cancer, carcinogenesis thereof can be delayed or hindered by the compound of the present invention or a salt thereof.

The medicament containing the compound of the present invention or a salt thereof is also effective for the prevention or treatment of a disease involving *Helicobacter pylori*. Examples of such a disease include digestive system cancer or pancreatitis resulting from hypergastrinemia caused by *Helicobacter pylori*, or inflammatory bowel diseases caused by *Helicobacter pylori*. In regard to the digestive system cancer, progress thereof can be delayed or hindered by the compound of the present invention or a salt thereof.

The present invention also provides a method for preventing or treating a disease involving *Helicobacter pylori* and/or gastric acid secretion, the method including administering an effective amount of the compound of the present invention or a salt thereof to a mammal in need of the method. The present invention also provides a use of the compound of the present invention or a salt thereof, for the production of a prophylactic or therapeutic agent for a disease involving *Helicobacter pylori* and/or gastric acid secretion.

The present invention also provides a method for preventing or treating a disease involving *Helicobacter pylori*, the method including administering an effective amount of the compound of the present invention or a salt thereof to a mammal in need of the method. The present invention also provides a use of the compound of the present invention or a salt thereof, for the production of a prophylactic or therapeutic agent for a disease involving *Helicobacter pylori*.

Upon using the compound of the present invention or a salt thereof as a medicine, various dosage forms can be employed in accordance with the purpose of prevention or treatment, and examples of the dosage forms may include oral solid preparations (for example, powders, fine granules, granules, tablets, coated tablets and capsules), oral liquid preparations (for example, dry syrups, syrups, internal liquid preparations and elixirs), injectable preparations (for example, subcutaneous, intramuscular and intravenous injectable preparations), and the like. These medicines may appropriate contain pharmaceutically acceptable excipients, carriers and the like, in addition to the active ingredients.

In the case of preparing an oral solid preparation, an excipient, and as necessary, a binder, a disintegrant, a gliding agent, a colorant, a savoring/flavoring agent, and the like can be added to the compound of the present invention, and then tablets, coated tablets, granules, powders, capsules and the like can be produced by routine methods. Such additives may be those generally used in the related art, and use may be made of, for example, as the excipient, cornstarch, lactose, sucrose, sodium chloride, mannitol, sorbitol, glucose, starch, calcium carbonate, kaolin, microcrystalline cellulose, silicic acid, and the like; and as the binder, water, ethanol, gum arabic, tragacanth, propanol, simple syrup, glucose solution, starch solution, gelatin solution, carboxymethyl cellulose, hydroxypropyl cellulose, gelatin, hydroxypropyl starch, methyl cellulose, ethyl cellulose, shellac, calcium phosphate, polyvinyl alcohol, polyvinyl ether, polyvinylpyrrolidone, and the like. It is allowed to add, as the disintegrant, powdered gelatin, crystalline cellulose, dry starch, sodium alginate, pectin, powdered agar, carboxymethyl cellulose, sodium hydrogen carbonate, calcium carbonate, calcium citrate, sodium lauryl sulfate, stearic acid monoglyceride, lactose, and the like; as the gliding agent, silica, purified talc, stearic acid salts, borax, polyethylene glycol, and the like; and as the colorant, titanium oxide, iron oxide, and the like. The savoring/flavoring agent may be exemplified by sucrose, orange peel, citric acid, tartaric acid, and the like.

In the case of preparing an oral liquid preparation, a savoring agent, a buffer, a stabilizer, a flavoring agent, and the like can be added to the compound of the present invention, and an internal liquid preparation, a syrup, an elixir and the like can be produced by routine methods. In this case, as the savoring/flavoring agent, the materials previously mentioned may be used, and there may be mentioned, as the buffer, sodium citrate, and the like; and as the stabilizer, tragacanth, gum arabic, gelatin, and the like.

In the case of preparing an injectable preparation, a pH adjusting agent, a buffer, a stabilizer, an isotonic agent, a local anesthetic agent and the like can be added to the compound of the present invention, and subcutaneous, intramuscular and intravenous injectable preparations can be produced by routine methods. As the pH adjusting agent and buffer in this case, sodium citrate, sodium acetate, sodium phosphate, and the like may be mentioned. As the stabilizer, sodium pyrosulfite, EDTA, thioglycolic acid, thiolactic acid, and the like may be mentioned. As the local anesthetic agent, procaine hydrochloride, lidocaine hydrochloride, and the like may be mentioned. As the isotonic agent, sodium chloride, glucose, and the like may be mentioned as examples.

The amount of the compound of the present invention that should be incorporated into each of the above-mentioned unit dosage forms is not constant, depending on the patient to whom this compound should be applied, or symptoms of the patient, or depending on the formulation; however, it is generally desirable to set the amount to about 1 to 1200 mg for oral preparations, and to about 0.1 to 500 mg for injectable preparations, per unit dosage form. Further, the daily amount of administration of a medicament having the above-mentioned dosage form varies with the symptoms, body weight, age, gender and the like of the patient, and thus cannot be determined collectively; however, the amount may be usually about 0.1 to 5000 mg, and preferably 1 to 1200 mg, per day for an adult, and it is preferable that this be administered once, or in about two to four divided portions, in one day.

Next, the raw material compounds used in the method of the present invention and the method for producing the compound of the present invention will be specifically described by way of Synthesis Examples and Examples, respectively, but the present invention is not intended to be limited thereto.

The HPLC analysis of the compound of Examples was carried out under the following conditions.

| | |
|---|---|
| Column | Inertsil ODS-3 150 mm × 4.6 mm ID |
| Eluent | 0.05 MK $H_2PO_4$/acetonitrile = 50/50 (v/v) |
| Flow rate | 1.0 mL/min |
| Column temperature | 40° C. |
| Injection amount | 2 μL |
| Detection wavelength | 254 nm |

Synthesis Example 1

Production of
4-methoxy-2,3-dimethylpyridine-1-oxide

To a solution prepared by diluting 41.6 g (2.0 eq.) of a 28% aqueous solution of sodium methoxide with 200 mL of dimethylsulfoxide, a liquid containing 17.0 g of 4-chlor-2,3-dimethylpyridine-1-oxide dissolved in dimethylsulfoxide (70 mL) was added dropwise. The mixture was allowed to react for 3 hours at 40 to 50° C., and then was left to stand overnight at room temperature. 15 mL of water was added to the reaction liquid, and the mixture was concentrated, to obtain a residue in the form of a black paste. Subsequently, the residue was dissolved in 500 mL of water, and then the aqueous solution was extracted three times with 670 mL of chloroform. The extract was dried over anhydrous magnesium sulfate, and then was concentrated to dryness under reduced pressure, to obtain 37.2 g of 4-methoxy-2,3-dimethylpyridine-1-oxide.

Synthesis Example 2

Production of
2-acetoxymethyl-3-methyl-4-methoxy-pyridine

To 37.2 g of 4-methoxy-2,3-dimethylpyridine-1-oxide, 55.0 g (5.0 eq.) of acetic anhydride was added, and the mixture was allowed to react for 3 hours at 90 to 100° C. Acetic anhydride was distilled off, and then the resulting concentrated residue was purified on a silica gel column, to obtain 15.8 g of 2-acetoxymethyl-3-methyl-4-methoxy-pyridine as an oily matter.

Synthesis Example 3

Production of 2-hydroxymethyl-3-methyl-4-methoxy-pyridine 15.8 g of 2-acetoxymethyl-3-methyl-4-methoxy-pyridine was added dropwise to a 25% aqueous solution of sodium hydroxide, and the mixture was allowed to react for one hour at room temperature. Subsequently, the reaction liquid was diluted with toluene, and then the toluene phase was washed with water, dried over anhydrous magnesium sulfate, and then concentrated, to obtain 5.7 g of 2-hydroxymethyl-3-methyl-4-methoxy-pyridine as an oily matter.

Synthesis Example 4

Production of 4-ethoxy-2,3-dimethylpyridine-1-oxide

To a solution prepared by diluting 8.6 g (2.0 eq.) of 60% sodium hydride with 200 mL of dimethylsulfoxide, 9.9 g (2.0 eq.) of anhydrous ethanol was added, and the mixture was allowed to react for one hour at 60° C. The reaction liquid was cooled to 30° C., and then a liquid containing 17.0 g of 4-chlor-2,3-dimethylpyridine-1-oxide dissolved in dimethylsulfoxide (70 mL) was added dropwise. The mixture was allowed to react for 2 hours at 40 to 50° C., and then was left to stand overnight at room temperature. 16 mL of water was added to the reaction liquid, and the mixture was concentrated, to obtain a residue in the form of a black paste. Subsequently, the residue was dissolved in 500 mL of water, and then the aqueous solution was extracted three times with 670 mL of chloroform. The extract was dried over anhydrous magnesium sulfate, and then was concentrated to dryness under reduced pressure. The obtained residue was purified on a silica gel column, to obtain 22.9 g of 4-ethoxy-2,3-dimethylpyridine-1-oxide.

Synthesis Example 5

Production of 2-acetoxymethyl-3-methyl-4-ethoxy-pyridine

To 22.9 g of 4-ethoxy-2,3-dimethylpyridine-1-oxide, 55.0 g (5.0 eq.) of acetic anhydride was added, and the mixture was allowed to react for 6 hours at 90 to 100° C. The acetic anhydride was distilled off, and the resulting concentrated residue was purified on a silica gel column, to obtain 28.2 g of 2-acetoxymethyl-3-methyl-4-ethoxy-pyridine as an oily matter.

Synthesis Example 6

Production of 2-hydroxymethyl-3-methyl-4-ethoxy-pyridine 28.2 g of 2-acetoxymethyl-3-methyl-4-ethoxy-pyridine was added dropwise to a 25% aqueous solution of sodium hydroxide, and the mixture was allowed to react for one hour at room temperature. Subsequently, the reaction liquid was diluted with toluene, and then the toluene phase was washed with water, dried over anhydrous magnesium sulfate, and then concentrated to dryness, to obtain 10.7 g of 2-hydroxymethyl-3-methyl-4-ethoxy-pyridine as an oily matter.

Synthesis Example 7

Production of 4-propoxy-2,3-dimethylpyridine-1-oxide

To a solution prepared by diluting 8.6 g (2.0 eq.) of 60% sodium hydroxide with 200 mL of dimethylsulfoxide, 13.0 g of 1-propanol (2.0 eq.) was added, and the mixture was allowed to react for one hour at 60° C. The reaction liquid was cooled to 30° C., and then a solution containing 17.0 g of 4-chlor-2,3-dimethylpyridine-1-oxide dissolved in dimethylsulfoxide (70 mL) was added dropwise. The mixture was allowed to react for 3 hours at 40 to 50° C., and then was left to stand overnight at room temperature. 15 mL of water was added to the reaction liquid, and the mixture was concentrated, to obtain a residue in the form of a black paste. Subsequently, the residue was dissolved in 500 mL of water, and then the aqueous solution was extracted three times with 670 mL of chloroform. The extract was dried over anhydrous magnesium sulfate, and then concentrated to dryness under reduced pressure, and the obtained residue was purified on a silica gel column, to obtain 20.3 g of 4-propoxy-2,3-dimethylpyridine-1-oxide.

Synthesis Example 8

Production of 2-acetoxymethyl-3-methyl-4-propoxy-pyridine

To 20.3 g of 4-propoxy-2,3-dimethylpyridine-1-oxide, 44.0 g (4.0 eq.) of acetic anhydride was added, and the mixture was allowed to react for 4 hours at 90° C. Acetic anhydride was distilled off, and then the resulting concentrated residue was purified on a silica gel column, to obtain 27.8 g of 2-acetoxymethyl-3-methyl-4-propoxy-pyridine as an oily matter.

Synthesis Example 9

Production of 2-hydroxymethyl-3-methyl-4-propoxy-pyridine 27.8 g of 2-acetoxymethyl-3-methyl-4-propoxy-pyridine was added dropwise into a 25% aqueous solution of sodium hydroxide, and the mixture was allowed to react for one hour at room temperature. Subsequently, the reaction liquid was diluted with toluene, and then the toluene phase was washed with water, dried over anhydrous magnesium sulfate, and then concentrated to dryness, to obtain 11.0 g of 2-hydroxymethyl-3-methyl-4-propoxy-pyridine as an oily matter.

Synthesis Example 10

Production of 4-butoxy-2,3-dimethylpyridine-1-oxide

To a solution prepared by diluting 8.6 g (2.0 eq.) of 60% sodium hydride with 200 mL of dimethylsulfoxide, 16.0 g (2.0 eq.) of 1-butanol was added, and the mixture was allowed to react for one hour at 60° C. The reaction liquid was cooled to 30° C., and then a liquid containing 17.0 g of 4-chlor-2,3-dimethylpyridine-1-oxide dissolved in dimethylsulfoxide (70 mL) was added dropwise. The mixture was allowed to react for 3 hours at 40 to 50° C., and was left to stand overnight at room temperature. 15 mL of water was added to the reaction liquid, and the mixture was concentrated, to obtain a residue in the form of a black paste. Subsequently, the residue was dissolved in 500 mL of water, and then the aqueous solution was extracted three times with 670 mL of chloroform. The extract was dried over anhydrous magnesium sulfate, and was concentrated to dryness under reduced pressure. The obtained residue was purified on a silica gel column, to obtain 20.3 g of 4-butoxy-2,3-dimethylpyridine-1-oxide.

Synthesis Example 11

Production of 2-acetoxymethyl-3-methyl-4-butoxy-pyridine

To 24.1 g of 4-butoxy-2,3-dimethylpyridine-1-oxide, 44.0 g (4.0 eq.) of acetic anhydride was added, and the mixture was allowed to react for 4 hours at 90° C. Acetic anhydride was distilled off, and then the resulting concentrated residue was purified on a silica gel column, to obtain 13.4 g of 2-acetoxymethyl-3-methyl-4-butoxy-pyridine as an oily matter.

Synthesis Example 12

Production of 2-hydroxymethyl-3-methyl-4-butoxy-pyridine 13.4 g of 2-acetoxymethyl-3-methyl-4-butoxy-pyridine was added dropwise to a 25% aqueous solution of sodium hydroxide, and the mixture was allowed to react for one hour at room temperature. The mixture was diluted with toluene, and then the toluene phase was washed with water, dried over anhydrous magnesium sulfate, and then concentrated to dryness, to obtain 8.3 g of 2-hydroxymethyl-3-methyl-4-butoxy-pyridine as an oily matter.

Synthesis Example 13

Production of 4-pentyloxy-2,3-dimethylpyridine-N-oxide 17.0 g (0.11 mol, 1.0 eq.) of 4-chlor-2,3-dimethylpyridine-N-oxide, 8.6 g (0.225 mol, 2.0 eq.) of caustic soda, and 19.0 g (0.22 mol, 2.0 eq.) of 1-pentanol were added to 68 mL of toluene, and the mixture as heated to reflux for 5 hours, and then cooled to room temperature. 15 mL of water was added to the reaction liquid, and the mixture was concentrated, to obtain a residue in the form of a black paste. Subsequently, the residue was dissolved in 500 mL of water, and then the aqueous solution was extracted three times with 670 mL of chloroform. The extract was dried over anhydrous magnesium sulfate, and then concentrated to dryness under reduced pressure, to obtain 28.8 g of 4-pentyloxy-2,3-dimethylpyridine-N-oxide.

Synthesis Example 14

Production of 4-pentyloxy-2-acetoxymethyl-3-methylpyridine

To 26.7 g (0.11 mol, 1.0 eq.) of 4-pentyloxy-2,3-dimethylpyridine-N-oxide, 44.0 g (0.43 mol, 4.0 eq.) of acetic anhydride was added, and the mixture was allowed to react for 7 hours at 90 to 100° C. Acetic anhydride was distilled off, and then the resulting concentrated residue was purified on a silica gel column, to obtain 22.0 g of 4-pentyloxy-2-acetoxymethyl-3-methylpyridine as an oily matter (yield 79.6%).

Synthesis Example 15

Production of 4-pentyloxy-2-hydroxymethyl-3-methylpyridine 22.0 g (0.088 mol, 1.0 eq.) of 4-pentyloxy-2-acetoxymethyl-3-methylpyridine was added dropwise to a 25% aqueous solution of sodium hydroxide, and the mixture was allowed to react for one hour at room temperature. Subsequently, the reaction liquid was diluted with toluene, and then the toluene phase was washed with water, dried over anhydrous magnesium sulfate, and then concentrated to dryness, to obtain 11.2 g of 4-pentyloxy-2-hydroxymethyl-3-methylpyridine as an oily matter (yield 60.8%).

Synthesis Example 16

Production of 4-hexyloxy-2,3-dimethylpyridine-N-oxide 15.8 g (0.1 mol, 1.0 eq.) of 4-chlor-2,3-dimethylpyridine-N-oxide, 8.0 g (0.2 mol, 2.0 eq.) of caustic soda, and 20.4 g (0.2 mol, 2.0 eq.) of 1-hexanol were added to 64 mL of toluene, and the mixture was heated to reflux for 4 hours, and then cooled to room temperature. 15 mL of water was added to the reaction liquid, and then the mixture was neutralized with concentrated hydrochloric acid (8 mL). Subsequently, the resultant was extracted three times with 670 mL of chloroform. The extract was dried over anhydrous magnesium sulfate, and then concentrated to dryness, to obtain 33.1 g of 4-hexyloxy-2,3-dimethylpyridine-N-oxide as a black brown oily matter.

Synthesis Example 17

Production of 4-hexyloxy-2-acetoxymethyl-3-methylpyridine

To 32.6 g (0.1 mol, 1.0 eq.) of 4-hexyloxy-2,3-dimethylpyridine-N-oxide, 40.8 g (0.4 mol, 4.0 eq.) of acetic anhydride was added, and the mixture was allowed to react for 5 hours at 87 to 93° C. Acetic anhydride was distilled off, and then the resulting concentrated residue was purified on a silica gel column, to obtain 17.6 g of 4-hexyloxy-2-acetoxymethyl-3-methylpyridine as an oily matter (yield 74.3%).

Synthesis Example 18

Production of 4-hexyloxy-2-hydroxymethyl-3-methylpyridine 17.3 g (0.065 mol, 1.0 eq.) of 4-hexyloxy-2-acetoxymethyl-3-methylpyridine was added dropwise to a 25% aqueous solution of sodium hydroxide at 5 to 22° C., and the mixture was allowed to react for one hour at room temperature, and then extracted with chloroform. The extract was washed with water, dried over anhydrous magnesium sulfate, and then concentrated to dryness, to obtain 12.7 g of 4-hexyloxy-2-hydroxymethyl-3-methylpyridine as a brown oily matter (yield 87.6%).

Synthesis Example 19

Production of
4-heptyloxy-2,3-dimethylpyridine-N-oxide 15.8 g (0.1 mol, 1.0 eq.) of 4-chlor-2,3-dimethylpyridine-N-oxide, 8.0 g (0.2 mol, 2.0 eq.) of caustic soda, and 23.2 g (0.2 mol, 2.0 eq.) of 1-heptanol were added to 64 mL of toluene, and the mixture was heated to reflux for 3 hours, and then cooled to room temperature. 15 mL of water was added to the reaction liquid, and then the mixture was neutralized with concentrated hydrochloric acid (8 mL). Subsequently, the resultant was extracted three times with 670 mL of chloroform. The extract was dried over anhydrous magnesium sulfate, and then concentrated under reduced pressure, to obtain 37.3 g of 4-heptyloxy-2,3-dimethylpyridine-N-oxide as a black brown oily matter.

Synthesis Example 20

Production of
4-heptyloxy-2-acetoxymethyl-3-methylpyridine

To 36.8 g (0.1 mol, 1.0 eq.) of 4-heptyloxy-2,3-dimethyll-pyridine-N-oxide, 40.8 g (0.4 mol, 4.0 eq.) of acetic anhydride was added, and the mixture was allowed to react for 5 hours at 87 to 93° C. Acetic anhydride was distilled off, and then the resulting concentrated residue was purified on a silica gel column, to obtain 19.5 g of 4-heptyloxy-2-acetoxymethyl-3-methylpyridine as an oily matter (yield 69.9%).

Synthesis Example 21

Production of
4-heptyloxy-2-hydroxymethyl-3-methylpyridine 19.0 g (0.068 mol, 1.0 eq.) of 4-heptyloxy-2-acetoxymethyl-3-methylpyridine was added dropwise to a 25% aqueous solution of sodium hydroxide at 13 to 25° C., and the mixture was allowed to react for one hour at room temperature, and then extracted with chloroform. The extract was washed with water, dried over anhydrous magnesium sulfate, and then concentrated to dryness, to obtain 15.0 g of 4-heptyloxy-2-hydroxymethyl-3-methylpyridine as a brown oily matter (yield 92.9%).

Synthesis Example 22

Production of
4-octyloxy-2,3-dimethylpyridine-N-oxide 15.8 g (0.1 mol, 1.0 eq.) of 4-chlor-2,3-dimethylpyridine-N-oxide, 8.0 g (0.2 mol, 2.0 eq.) of caustic soda, and 26.0 g (0.2 mol, 2.0 eq.) of 1-octanol were added to 64 mL of toluene, and the mixture was heated to reflux for 3 hours, and then cooled to room temperature. 15 mL of water was added to the reaction liquid, and then the mixture was neutralized with concentrated hydrochloric acid (8 mL). Subsequently, the resultant was extracted three times with 670 mL of chloroform. The extract was dried over anhydrous magnesium sulfate, and then concentrated to dryness under reduced pressure, to obtain 39.2 g of 4-octyloxy-2,3-dimethylpyridine-N-oxide as a black brown oily matter.

Synthesis Example 23

Production of
4-octyloxy-2-acetoxymethyl-3-methylpyridine

To 38.7 g (0.1 mol, 1.0 eq.) of 4-octyloxy-2,3-dimethylpyridine-N-oxide, 40.8 g (0.4 mol, 4.0 eq.) of acetic anhydride was added, and the mixture was allowed to react for 5 hours at 88 to 92° C. Acetic anhydride was distilled off, and then the resulting concentrated residue was purified on a silica gel column, to obtain 17.6 g of 4-octyloxy-2-acetoxymethyl-3-methylpyridine as an oily matter (yield 60.0%).

Synthesis Example 24

Production of
4-octyloxy-2-hydroxymethyl-3-methylpyridine 17.3 g (0.059 mol, 1.0 eq.) of 4-octyloxy-2-acetoxymethyl-3-methylpyridine was added dropwise to a 25% aqueous solution of sodium hydroxide at 11 to 22° C., and the mixture was allowed to react for one hour at room temperature, and then extracted with chloroform. The extract was washed with water, dried over magnesium sulfate, and then concentrated to dryness, to obtain 12.2 g of 4-octyloxy-2-hydroxymethyl-3-methylpyridine as a pale brown oily matter (yield 82.3%).

Synthesis Example 25

Production of
4-nonyloxy-2,3-dimethylpyridine-N-oxide 15.8 g (0.1 mol, 1.0 eq.) of 4-chlor-2,3-dimethylpyridine-N-oxide, 8.0 g (0.2 mol, 2.0 eq.) of caustic soda, and 28.9 g (0.2 mol, 2.0 eq.) of 1-nonanol were added to 64 mL of toluene, and the mixture was heated to reflux for 4 hours, and then cooled to room temperature. 160 mL of water was added to the reaction liquid, and then the mixture was neutralized with concentrated hydrochloric acid (8.5 g). Subsequently, the resultant was extracted with 160 mL of ethyl acetate. The extract was dried over anhydrous magnesium sulfate, and then concentrated under reduced pressure, to obtain 42.4 g of 4-nonyloxy-2,3-dimethylpyridine-N-oxide as a black brown oily matter.

Synthesis Example 26

Production of
4-nonyloxy-2-acetoxymethyl-3-methylpyridine

To 41.4 g (0.1 mol, 1.0 eq.) of 4-nonyloxy-2,3-dimethylpyridine, 40.8 g (0.4 mol, 4.0 eq.) of acetic anhydride was added, and the mixture was allowed to react for 7 hours at 88 to 92° C. Acetic anhydride was distilled off, and then the resulting concentrated residue was purified on a silica gel column, to obtain 16.7 g of 4-nonyloxy-2-acetoxymethyl-3-methylpyridine as a black brown oily matter (total yield of two processes 54.4%).

Synthesis Example 27

Production of
4-nonyloxy-2-hydroxymethyl-3-methylpyridine 15.4 g (0.05 mol, 1.0 eq.) of 4-nonyloxy-2-acetoxymethyl-3-methylpyridine was added dropwise to a 20% aqueous solution of sodium hydroxide (20.0 g) at 11 to 21° C., and the mixture was allowed to react for one hour at room temperature, and then extracted with water (77 mL) and toluene (128 mL). The extract was washed with water, dried over anhydrous magnesium sulfate, and then concentrated to dryness, to obtain 16.8 g of 4-nonyloxy-2-hydroxymethyl-3-methylpyridine as a brown oily matter.

Synthesis Example 28

Production of 4-decyloxy-2,3-dimethylpyridine-N-oxide 15.8 g (0.1 mol, 1.0 eq.) of 4-chlor-2,3-dimethylpyridine-N-oxide, 8.0 g (0.2 mol, 2.0 eq.) of caustic soda, and 28.5 g of 1-decanol (0.18 mol, 1.8 eq.) were added to 64 mL of toluene, and the mixture was heated to reflux for 4 hours, and then cooled to room temperature. 160 mL of water was added to the reaction liquid, and then the mixture was neutralized with concentrated hydrochloric acid (7.3 g). Subsequently, the resultant was extracted with 100 mL of ethyl acetate. The extract was dried over anhydrous magnesium sulfate, and then concentrated to dryness under reduced pressure, to obtain 42.2 g of 4-decyloxy-2,3-dimethylpyridine-N-oxide as a black brown oily matter.

Synthesis Example 29

Production of 4-decyloxy-2-acetoxymethyl-3-methylpyridine

To 41.2 g (0.1 mol, 1.0 eq.) of 4-decyloxy-2,3-dimethylpyridine-N-oxide, 40.8 g (0.4 mol, 4.0 eq.) of acetic anhydride was added, and the mixture was allowed to react for 8.5 hours at 88 to 92° C. Acetic anhydride was distilled off, and then the resulting concentrated residue was purified on a silica gel column, to obtain 19.8 g of 4-decyloxy-2-acetoxymethyl-3-methylpyridine as a black brown oily matter (total yield of two processes 61.7%).

Synthesis Example 30

Production of 4-decyloxy-2-hydroxymethyl-3-methylpyridine 18.6 g (0.058 mol, 1.0 eq.) of 4-decyloxy-2-acetoxymethyl-3-methylpyridine was added dropwise to a 20% aqueous solution of sodium hydroxide (23 g) at 11 to 22° C., and the mixture was allowed to react for one hour at room temperature. Subsequently, water (93 mL) was added, and then the mixture was extracted with toluene (130 mL). The extract was washed with water, dried over anhydrous magnesium sulfate, and then concentrated to dryness, to obtain 20.6 g of 4-decyloxy-2-hydroxymethyl-3-methylpyridine as a brown oily matter.

Example 1

Hereinafter, the present invention will be specifically described by way of Examples of the present invention.

Production of 2-[(4-n-pentyloxy-3-methylpyridin-2-yl)-methylthio]-1H-benz imidazole 11.0 g (0.054 mol, 1.0 eq.) of 4-pentyloxy-2-hydroxymethyl-3-methylpyridine was dissolved in 620 mL of chloroform, and 24.9 g (0.281 mol, 4 eq.) of thionyl chloride was added dropwise at 22 to 30° C. Subsequently, the mixture was heated to reflux for one hour, and then concentrated, to obtain 4-pentyloxy-2-chloromethyl-3-methylpyridine as a brown oily matter.

To a liquid prepared by dissolving with stirring 7.5 g (0.052 mol, 1.0 eq.) of 2-mercaptobenzimidazole and 61.5 g (0.319 mol, 5.8 eq.) of a 28% sodium methoxide solution in 120 mL of methanol, a liquid prepared by dissolving the whole amount of 4-pentyloxy-2-chloromethyl-3-methylpyridine in 180 mL of methanol was added at 30° C. Subsequently, the mixture was heated to reflux for one hour and cooled, and then methanol was solid dried under reduced pressure. A yellow brown oily residue resulting therefrom was dissolved in 250 mL of ethyl acetate, and then the organic layer was washed with 100 mL of water. The organic layer was dried over anhydrous magnesium sulfate, and then concentrated to dryness. The resulting residue was purified by silica gel column chromatography, and then was concentrated to dryness, to obtain 6.9 g of amorphous solidified product. The product was recrystallized from an ethyl acetate/1-hexane mixed liquid, to obtain 4.3 g of colorless crystals (HPLC: 98.5 Area %, yield 10.6%).

$^1$H-NMR (400 MHz, CDCl$_3$) δ: 0.94 (3H, t J=6 Hz), 1.37-1.48 (4H, m), 1.80-1.86 (2H, m), 2.26 (3H, s), 4.02 (2H, t J=6 Hz), 4.37 (2H, s), 6.73 (1H, d J=6 Hz), 7.17-7.18 (2H, m), 7.53 (2H, m), 8.33 (1H, d J=6 Hz), 13.04 (1H, bs)

MS m/z: 341 (M$^+$)

Example 2

Production of 2-[(4-n-hexyloxy-3-methylpyridin-2-yl)-methylthio]-1H-benzimidazole 12.2 g (0.055 mol, 1.0 eq.) of 4-hexyloxy-2-hydroxymethyl-3-methylpyridine was dissolved in 620 mL of chloroform, and 33.4 g (0.281 mol, 5.1 eq.) of thionyl chloride was added dropwise at 23 to 29° C. Subsequently, the mixture was heated to reflux for one hour and then concentrated, to obtain 24.7 g of 4-hexyloxy-2-chloromethyl-3-methylpyridine as a brown oily matter.

To a liquid prepared by dissolving with stirring 7.8 g (0.052 mol, 0.95 eq.) of 2-mercaptobenzimidazole and 61.5 g (0.319 mol, 5.8 eq.) of a 28% sodium methoxide solution in 360 mL of methanol, a liquid prepared by dissolving the whole amount of 4-hexyloxy-2-chloromethyl-3-methylpyridine in 180 mL of methanol was added at 30° C. Subsequently, the mixture was heated to reflux for 30 minutes and cooled, and then methanol was solid dried under reduced pressure. A yellow brown oily residue resulting therefrom was dissolved in 200 mL of ethyl acetate, and then the organic layer was washed with 80 mL of water. The organic layer was dried over anhydrous magnesium sulfate, and then concentrated to dryness. The resulting residue was purified by silica gel column chromatography, and then was concentrated to dryness, to obtain 15.2 g of an orange-colored oily matter. The product was recrystallized from ethyl acetate (5 vol.), to obtain 5.0 g of colorless crystals (HPLC: 99.1 Area %, yield 25.5%).

$^1$H-NMR (400 MHz, CDCl$_3$) δ: 0.91 (3H, t J=7 Hz), 1.34-1.37 (4H, m), 1.44-1.50 (2H, m), 1.79-1.86 (2H, m), 2.26 (3H, s), 4.02 (2H, t J=6 Hz), 4.37 (2H, s), 6.73 (1H, d J=6 Hz), 7.15-7.20 (2H, m), 7.45-7.62 (2H, m), 8.34 (1H, d J=6 Hz), 13.04 (1H, bs)

MS m/z: 355 (M$^+$)

Example 3

Production of 2-[(4-n-heptyloxy-3-methylpyridin-2-yl)-methylthio]-1H-benz imidazole 14.5 g (0.061 mol, 1.0 eq.) of 4-heptyloxy-2-hydroxymethyl-3-methylpyridine was dissolved in 700 mL of chloroform, and 37.0 g (0.311 mol, 5.1 eq.) of thionyl chloride was added dropwise at 22 to 30° C. Subsequently, the mixture was heated to reflux for 30 minutes and then concentrated, to obtain 28.2 g of 4-heptyloxy-2-chloromethyl-3-methylpyridine as a black oily matter.

To a liquid prepared by dissolving with stirring 8.7 g (0.058 mol, 0.95 eq.) of 2-mercaptobenzimidazole and 68.2 g (0.354 mol, 5.8 eq.) of a 28% sodium methoxide solution in 400 mL of methanol, a liquid prepared by dissolving the whole amount of 4-heptyloxy-2-chloromethyl-3-methylpyridine in 210 mL of methanol was added at 28° C. Subsequently, the mixture was heated to reflux for one hour and cooled, and then methanol was solid dried under reduced pressure. A yellow brown oily residue resulting therefrom was dissolved in 250 mL of ethyl acetate, and then the organic layer was washed with 100 mL of water. The organic layer was dried over anhydrous magnesium sulfate, and then concentrated to dryness. The resulting residue was purified by silica gel column chromatography, and then was concentrated to dryness, to obtain 17.8 g of an orange-colored oily matter. The orange-colored oily matter was recrystallized from ethyl acetate (7 vol.), to obtain 8.7 g of colorless crystals (HPLC: 99.0 Area %, yield 38.7%).

$^1$H-NMR (400 MHz, CDCl$_3$) δ: 0.90 (3H, t J=6 Hz), 1.29-1.40 (6H, m), 1.44-1.51 (2H, m), 1.80-1.86 (2H, m), 2.26 (3H, s), 4.02 (2H, t J=6 Hz), 4.37 (2H, s), 6.73 (1H, d J=6 Hz), 7.15-7.20 (2H, m), 7.45-7.62 (2H, m), 8.34 (1H, d J=6 Hz), 13.04 (1H, bs)

MS m/z: 369 (M$^+$)

Example 4

Production of 2-[(4-n-butoxy-3-methylpyridin-2-yl)-methylthio]-1H-benzimidazole 8.3 g of 2-acetoxymethyl-3-methyl-4-butoxy-pyridine was dissolved in chloroform, and 21.6 g (4 eq.) of thionyl chloride was added. The mixture was heated to reflux for one hour and then concentrated, and a residue resulting therefrom was dissolved in methanol. The solution was added in advance to 6.1 g (1 eq.) of 2-mercaptobenzimidazole, 230 mL of a 28% sodium methoxide solution, and 120 mL of methanol, and the mixture was heated to reflux for one hour. Methanol was distilled off, ice was added to the residue, and the mixture was extracted with ethyl acetate. The ethyl acetate layer was dried over anhydrous magnesium sulfate. Subsequently, the ethyl acetate solution was concentrated to dryness, and the resulting residue was purified by silica gel column chromatography, and then was concentrated to dryness, to obtain 12.2 g of yellow crystals. 12.2 g of the crystals were recrystallized from ethyl acetate/1-hexane, to obtain 4.2 g of colorless crystals. Total yield 10.8% (purity by HPLC: 97.0%).

$^1$H-NMR (400 MHz, CDCl$_3$) δ: 0.99 (3H, t J=7 Hz), 1.51-1.56 (2H, m), 1.78-1.85 (2H, m), 2.26 (3H, s), 4.03 (2H, t J=7 Hz), 4.37 (2H, s), 6.74 (1H, d J=6 Hz), 7.17-7.19 (2H, m), 7.54 (2H, m), 8.34 (1H, d J=6 Hz), 13.04 (1H, bs)

MS m/z: 327 (M$^+$)

Example 5

Production of 2-[(4-n-octyloxy-3-methylpyridin-2-yl)-methylthio]-1H-benzimidazole 11.8 g (0.047 mol, 1.0 eq.) of 4-octyloxy-2-hydroxymethyl-3-methylpyridine was dissolved in 600 mL of chloroform, and 28.6 g (0.240 mol, 5.1 eq.) of thionyl chloride was added dropwise at 19 to 27° C. Subsequently, the mixture was heated to reflux for one hour and then concentrated, to obtain 23.8 g of 4-octyloxy-2-chloromethyl-3-methylpyridine as a black oily matter.

To a liquid prepared by dissolving with stirring 6.7 g (0.045 mol, 0.95 eq.) of 2-mercaptobenzimidazole and 52.5 g (0.273 mol, 5.8 eq.) of a 28% sodium methoxide solution in 350 mL of methanol, a liquid prepared by dissolving the whole amount of 4-octyloxy-2-chloromethyl-3-methylpyridine in 180 mL of methanol was added at 27° C. Subsequently, the mixture was heated to reflux for one hour and cooled, and then methanol was solid dried under reduced pressure. A brown oily residue resulting therefrom was dissolved in 250 mL of ethyl acetate, and then the organic layer was washed with 100 mL of water. The organic layer was dried over anhydrous magnesium sulfate, and then concentrated to dryness. The resulting residue was purified by silica gel column chromatography, and then was concentrated to dryness, to obtain 14.9 g of an orange-colored oily matter. The orange-colored oily matter was recrystallized from ethyl acetate (5 vol.), to obtain 5.8 g of colorless crystals (HPLC: 98.8 Area %, yield 32.2%).

$^1$H-NMR (400 MHz, CDCl$_3$) δ: 0.89 (3H, t J=6 Hz), 1.29-1.35 (8H, m), 1.44-1.49 (2H, m), 1.79-1.85 (2H, m), 2.26 (3H, s), 4.02 (2H, t J=6 Hz), 4.37 (2H, s), 6.73 (1H, d J=6 Hz), 7.16-7.20 (2H, m), 7.45-7.62 (2H, m), 8.34 (1H, d J=6 Hz), 13.04 (1H, bs)

MS m/z: 383 (M$^+$)

Next, Production Examples for the compounds used as Comparative Examples will be shown as Reference Examples.

Reference Example 1

Production of 2-[(4-methoxy-3-methylpyridin-2-yl)-methylthio]-1H-benzimidazole 5.7 g of 2-acetoxymethyl-3-methyl-4-methoxy-pyridine was dissolved in chloroform, and 18 g (4 eq.) of thionyl chloride was added. The mixture was heated to reflux for one hour and then concentrated, and a residue resulting therefrom was dissolved in methanol. The solution was added in advance to 5.3 g (1 eq.) of 2-mercaptobenzimidazole, 45 mL of a 28% sodium methoxide solution, and 100 mL of methanol, and the mixture was heated to reflux for one hour. Methanol was distilled off, and ice and ethyl acetate were added to the residue, to wash the residue by suspending. Produced crystals were collected by filtration, and then were washed by suspending in water, to obtain 7.1 g of colorless crystals. Total yield 20.9% (purity by HPLC: 98.2%).

$^1$H-NMR (400 MHz, CDCl$_3$) δ: 2.27 (3H, s), 3.89 (3H, s), 4.40 (2H, s), 6.76 (1H, d J=6 Hz), 7.16-7.20 (2H, m), 7.44-7.63 (2H, m), 8.36 (1H, d J=6 Hz), 12.96 (1H, bs)

MS m/z: 285 (M$^+$)

Reference Example 2

Production of 2-[(4-ethoxy-3-methylpyridin-2-yl)-methylthio]-1H-benzimidazole 10.7 g of 2-acetoxymethyl-3-methyl-4-ethoxy-pyridine was dissolved in chloroform, and 28.2 g (4 eq.) of thionyl chloride was added. The mixture was heated to reflux for one hour and then concentrated, and a residue resulting therefrom was dissolved in methanol. The solution was added in advance to 8.4 g (1 eq.) of 2-mercaptobenzimidazole, 71 mL of a 28% sodium methoxide solution, and 150 mL of methanol, and the mixture was heated to reflux for one hour. Methanol was distilled off, and ice and ethyl acetate were added to the residue, to wash the residue by suspending. Produced crystals were collected by filtration and dissolved in methanol, and the solution was dried over anhydrous magnesium sulfate. Subsequently, the methanol solution was concentrated to dryness, and the resultant was dissolved in chloroform. The chloroform layer was dried over magnesium sulfate and then concentrated to dryness, to obtain an amorphous solid. The solid was washed by suspending in ethyl acetate, to obtain 2.8 g of colorless crystals. Total yield 7.9% (purity by HPLC: 98.2%).

$^1$H-NMR (400 MHz, CDCl$_3$) δ: 1.43 (3H, t J=7 Hz), 2.28 (3H, s), 4.11 (2H, q J=7 Hz), 4.37 (2H, s), 6.73 (1H, d J=6 Hz), 7.16-7.20 (2H, m), 7.44-7.63 (2H, m), 8.33 (1H, d J=6 Hz), 13.01 (1H, bs)

MS m/z: 299 (M$^+$)

Reference Example 3

Production of 2-[(4-n-propoxy-3-methylpyridin-2-yl)-methylthio]-1H-benzimidazole 11.0 g of 2-acetoxymethyl-3-methyl-4-propoxy-pyridine was dissolved in chloroform, and 30 g (4 eq.) of thionyl chloride was added. The mixture was heated to reflux for one hour and then concentrated, and a residue resulting therefrom was dissolved in methanol. The solution was added in advance to 8.7 g (1 eq.) of 2-mercaptobenzimidazole, 73 mL of a 28% sodium methoxide solution, and 300 mL of methanol, and the mixture was heated to reflux for one hour. Methanol was distilled off, ice was added to the residue, and the mixture was extracted with ethyl acetate. The ethyl acetate layer was dried over anhydrous magnesium sulfate. Subsequently, the ethyl acetate solution was concentrated to dryness, and the resulting residue was purified by silica gel column chromatography, and then was concentrated to dryness, to obtain 15.5 g of yellow crystals. The yellow crystals were recrystallized from ethyl acetate, to obtain 6.3 g of colorless crystals. Total yield 17% (purity by HPLC: 98.1%).

$^1$H-NMR (400 MHz, CDCl$_3$) δ: 1.07 (3H, t J=7 Hz), 1.83-1.89 (2H, m), 2.27 (3H, s), 3.99 (2H, t J=7 Hz), 4.37 (2H, s), 6.73 (1H, d J=6 Hz), 7.17-7.20 (2H, m), 7.44-7.62 (2H, m), 8.35 (1H, d J=6 Hz), 13.02 (1H, bs)

MS m/z: 313 (M$^+$)

Reference Example 4

Production of 2-[(4-n-nonyloxy-3-methylpyridin-2-yl)-methylthio]-1H-benzimidazole 16.0 g (0.05 mol, 1.0 eq.) of 4-nonyloxy-2-hydroxymethyl-3-methylpyridine was dissolved in 320 mL of ethyl acetate, and 6.5 g (0.055 mol, 1.1 eq.) of thionyl chloride was added dropwise at 8 to 12° C. Subsequently, the mixture was allowed to react for 0.5 hours at room temperature, and then a 7% aqueous solution of sodium bicarbonate (200 g) was added to adjust the reaction liquid to pH 7.5. The organic layer was washed with a 5% aqueous solution of sodium bicarbonate (160 g), dried over anhydrous magnesium sulfate, and then concentrated to dryness under reduced pressure, to obtain 12.8 g of 4-nonyloxy-2-chloromethyl-3-methylpyridine as a black oily matter.

To a liquid prepared by dissolving with stirring 5.7 g (0.038 mol, 0.9 eq.) of 2-mercaptobenzimidazole and 9.7 g (0.0504 mol, 1.2 eq.) of a 28% sodium methoxide solution in 120 mL of methanol, a liquid containing 12.0 g of 4-nonyloxy-2-chloromethyl-3-methylpyridine dissolved in 60 mL of methanol was added at 29° C. Subsequently, the mixture was heated to reflux for 0.5 hours and cooled, and then methanol was solid dried under reduced pressure. A brown oily residue resulting therefrom was dissolved in 240 mL of ethyl acetate, and then the organic layer was washed with 120 mL of water. 36 g of silica gel was added with stirring to the organic layer, subsequently the silica gel was removed by filtration, and then the filtrate was concentrated to dryness under reduced pressure, to obtain 16.4 g of pale green brown crystals. The pale green brown crystals were recrystallized from ethyl acetate (10 vol.), to obtain 5.5 g of pale brown crystals (HPLC: 98.8 Area %, yield 32.9%).

$^1$H-NMR (400 MHz, CDCl$_3$) δ: 0.89 (3H, t J=6 Hz), 1.29-1.35 (8H, m), 1.44-1.49 (2H, m), 1.79-1.85 (2H, m), 2.26 (3H, s), 4.02 (2H, t J=6 Hz), 4.37 (2H, s), 6.73 (1H, d J=6 Hz), 7.16-7.20 (2H, m), 7.45-7.62 (2H, m), 8.34 (1H, d J=6 Hz), 13.04 (1H, bs)

MS m/z: 397 (M$^+$)

Reference 5

Production of 2-[(4-n-decyloxy-3-methylpyridin-2-yl)-methylthio]-1H-benzimidazole 19.8 g (0.058 mol, 1.0 eq.) of 4-decyloxy-2-hydroxymethyl-3-methylpyridine was dissolved in 300 mL of ethyl acetate, and 7.6 g (0.064 mol, 1.1 eq.) of thionyl chloride was added dropwise at 12 to 18° C. Subsequently, the mixture was allowed to react for 0.5 hours at room temperature, and then a 7% aqueous solution of sodium bicarbonate (220 g) was added to adjust the reaction liquid to pH 7.5. The organic layer was washed with a 5% aqueous solution of sodium bicarbonate (160 g), dried over anhydrous magnesium sulfate, and then concentrated to dryness under reduced pressure, to obtain 15.8 g of 4-decyloxy-2-chloromethyl-3-methylpyridine as a black oily matter.

To a liquid prepared by dissolving with stirring 6.8 g (0.045 mol, 0.9 eq.) of 2-mercaptobenzimidazole and 11.6 g (0.06 mol, 1.2 eq.) of a 28% sodium methoxide solution in 150 mL of methanol, a liquid containing 15.0 g of 4-decyloxy-2-chloromethyl-3-methylpyridine dissolved in 75 mL of methanol was added at 30° C. Subsequently, the mixture was heated to reflux for 0.5 hours and cooled, and then methanol was solid dried under reduced pressure. An orange-colored oily residue resulting therefrom was dissolved in 300 mL of ethyl acetate, and then the organic layer was washed with 150 mL of water. 45 g of silica gel was added with stirring to the organic layer, subsequently the silica gel was removed by filtration, and then the filtrate was concentrated to dryness under reduced pressure, to obtain 18.5 g of pale orange crystals. The pale orange crystals were recrystallized from ethyl acetate (10 vol.), to obtain 9.7 g of pale orange crystals (HPLC: 99.6 Area %, yield 47.1%).

$^1$H-NMR (400 MHz, CDCl$_3$) δ: 0.89 (3H, t J=6 Hz), 1.29-1.35 (8H, m), 1.44-1.49 (2H, m), 1.79-1.85 (2H, m), 2.26 (3H, s), 4.02 (2H, t J=6 Hz), 4.37 (2H, s), 6.73 (1H, d J=6 Hz), 7.16-7.20 (2H, m), 7.45-7.62 (2H, m), 8.34 (1H, d J=6 Hz), 13.04 (1H, bs)

MS m/z: 411 (M$^+$)

Reference Example 6

Production of (±)-2-[(4-n-pentyloxy-3-methylpyridin-2-yl)-methylsulfinyl]-1H-benzimidazole 3.00 g (8.8 mmol, 1.0 eq.) of 2-[(4-pentyloxy-3-methylpyridin-2-yl)-methylthio]-1H-benzimidazole was dissolved in 24.5 mL of dichloromethane, and the mixture was cooled to −10° C. or below under a nitrogen atmosphere. Subsequently, a solution of 2.01 g (9.9 mmol, 1.1 eq.) of m-chloroperbenzoic acid (85% purity) dissolved in 19.4 mL of dichloromethane was added dropwise over one hour at −10° C. or below. While the temperature was maintained at −10° C. or below, the mixture was stirred for 2.5 hours. Since the reaction was not completed, a solution of 0.45 g (2.2 mmol, 0.3 eq.) of m-chloroperbenzoic acid (85% purity) in 5.0 mL of dichloromethane was further added at −10° C. or below, and the mixture was further stirred for one hour at −10° C. or below. After the temperature of the liquid had reached 20° C., 9.41 g of a 10% aqueous solution of sodium hydroxide and 36 mL of water were added to adjust the aqueous layer to pH 13.04. With the dichloromethane layer removed, the aqueous layer was adjusted to pH 10.49 by adding 11.21 g of a 10% aqueous solution of ammonium acetate, and then was extracted with 50 mL of dichloromethane. The organic layer was concentrated under reduced pressure at 40° C. or below, and then a mixed liquid of 1.35 g of acetone and 27.0 g of n-hexane was added. A solid precipitated therefrom was collected by filtration, to obtain 1.86 g of (±)-2-[(4-n-pentyloxy-3-methylpyridin-2-yl)-methylsulfinyl]-1H-benzimidazole as a grey green amorphous powder (HPLC: 97.7 Area %, yield 59.2%).

$^1$H-NMR (400 MHz, CDCl$_3$) δ: 0.94 (3H, t J=7 Hz), 1.35-1.45 (4H, m), 1.76-1.81 (2H, m), 2.13 (3H, s), 3.97 (2H, t J=6 Hz), 4.71 (1H, d J=14 Hz), 4.82 (1H, d J=14 Hz), 6.69 (1H, d J=6 Hz), 7.33-7.28 (2H, m), 7.63 (2H, m), 8.30 (1H, d J=6 Hz) MS m/z: 357 (M$^+$)

Reference Example 7

Production of (±)-2-[(4-n-hexyloxy-3-methylpyridin-2-yl)-methylsulfinyl]-1H-benzimidazole 1.00 g (2.8 mmol, 1.0 eq.) of 2-[(4-hexyloxy-3-methylpyridin-2-yl)-methylthio]-1H-benzimidazole was dissolved in 7.8 mL of dichloromethane, and the mixture was cooled to −18° C. or below under a nitrogen atmosphere. Subsequently, a solution of 0.63 g (3.1 mmol, 1.1 eq.) of m-chloroperbenzoic acid (85% purity) dissolved in 6.2 mL of dichloromethane was added dropwise over 0.5 hours at −18° C. or below. While the temperature was maintained at −18° C. or below, the mixture was stirred for one hour. After the temperature of the liquid had reached 20° C., 4.77 g of a 10% aqueous solution of sodium hydroxide and 22 mL of water were added to adjust the aqueous layer to pH 13.11. With the dichloromethane layer removed, the aqueous layer was adjusted to pH 10.47 by adding 16.56 g of a 10% aqueous solution of ammonium acetate, and then was extracted with 30 mL of dichloromethane. The organic layer was concentrated under reduced pressure at 40° C. or below to obtain a concentrate, and then 20 mL of n-hexane was added to solidify the concentrate. Subsequently, the solid was collected by filtration, to obtain 0.538 g of (±)-2-[(4-n-hexyloxy-3-methylpyridin-2-yl)-methylsulfinyl]-1H-benzimidazole as a grey green amorphous powder (HPLC: 97.3 Area %, yield 51.5%).

$^1$H-NMR (400 MHz, CDCl$_3$) δ: 0.91 (3H, t J=7 Hz), 1.32-1.47 (6H, m), 1.75-1.82 (2H, m), 2.16 (3H, s), 3.97 (2H, t J=6 Hz), 4.70 (1H, d J=14 Hz), 4.82 (1H, d J=14 Hz), 6.70 (1H, d J=6 Hz), 7.29-7.33 (2H, m), 7.63 (2H, m), 8.30 (1H, d J=6 Hz) MS m/z: 371 (M$^+$)

Reference Example 8

Production of (±)-2-[(4-n-heptyloxy-3-methylpyridin-2-yl)-methylsulfinyl]-1H-benzimidazole 1.00 g (2.7 mmol, 1.0 eq.) of 2-[(4-heptyloxy-3-methylpyridin-2-yl)-methylthio]-1H-benzimidazole was dissolved in 7.6 mL of dichloromethane, and the mixture was cooled to −20° C. or below under a nitrogen atmosphere. Subsequently, a solution of 0.61 g (5.8 mmol, 2.1 eq.) of m-chloroperbenzoic acid dissolved in 6.0 mL of dichloromethane was added dropwise over 0.5 hours at −20° C. or below. While the temperature was maintained at −20° C. or below, the mixture was stirred for 40 minutes. After the temperature of the liquid had reached 20° C., 6.0 g of a 10% aqueous solution of sodium hydroxide and 30 mL of water were added to adjust the aqueous layer to pH 13.16. With the dichloromethane layer removed, the aqueous layer was further washed with 12 mL of dichloromethane. Subsequently, 30 mL of fresh dichloromethane was added, and then 9.42 g of a 10% aqueous solution of ammonium acetate was added to adjust the pH of the aqueous layer to pH 10.44. The organic layer was washed with 12 mL of water, and then was concentrated under reduced pressure at 40° C. or below to obtain a concentrate. 20 mL of n-hexane was added to solidify the concentrate, and then the solid was collected by filtration, to obtain 0.729 g of (±)-2-[(4-n-heptyloxy-3-methylpyridin-2-yl)-methylsulfinyl]-1H-benzimidazole as a grey green amorphous powder (HPLC: 97.4 Area %, yield 69.8%).

Stability Test

A test for the stability of thioether compounds (hereinafter, referred to SH-form) and sulfoxide compounds (hereinafter, referred to SO-form) at pH 2.0 was carried out.

(Method) Each of the specimens produced in Examples 1 to 3 and Reference Examples 6 to 8 (sulfinyl products of Examples 1 to 3) was maintained in a solution adjusted to pH 2 with 0.5 or 1.0 mmol/L HCl (37° C.) for a predetermined time period. Subsequently, the solution was adjusted to pH 8 with triethylamine, and then an HPLC analysis was performed to calculate the residual ratio.

The results are presented in Table 1 and FIG. 1 in terms of stability in an acidic hydrochloric acid solution (pH 2).

TABLE 1

| | | Stability against acid | | |
|---|---|---|---|---|
| | Number of carbon | | Residual ratio at pH 2 | |
| n | atoms of R | 0 min | 30 min | 2 hours |
| 0 (—S—) | 5 (Example 1) | 100 | 100 | 100 |
| | 6 (Example 2) | 100 | 100 | 100 |
| | 7 (Example 3) | 100 | 100 | 100 |
| 1 (—S=O) | 5 (oxide of Example 1) | 100 | 0 | 0 |
| | 6 (oxide of Example 2) | 100 | 0 | 0 |
| | 7 (oxide of Example 3) | 100 | 0 | 0 |
| Existing PPI | OMZ | 100 | 0 | 0 |
| | LAZ | 100 | 0 | 0 |
| | RAZ | 100 | 0 | 0 |

OMZ: Omeprazole,
LAZ: Lansoprazole,
RAZ: Rabeprazole

In the table, OMZ indicates omeprazole, LAZ indicates lansoprazole, and RAZ indicates rabeprazole. The "oxide of Example 1" is the compound shown in Reference Example 6, the "oxide of Example 2" is the compound shown in Reference Example 7, and the "oxide of Example 3" is the compound shown in Reference Example 8.

The vertical axis of FIG. 1 represents stability (residual ratio) (%), while the horizontal axis represents time elapsed (minutes). In FIG. 1, the black diamond-shaped mark (dark blue in the original diagram) indicates the case of the compound of Example 1; the black rectangle mark (red in the original diagram) indicates the case of the compound of Example 2; the white triangle mark (yellow in the original diagram) indicates the case of the compound of Example 3; the grey X mark (blue in the original diagram) indicates the case of the compound of Reference Example 6; the black X mark (red in the original diagram) indicates the case of the compound of Reference Example 7; the black circle mark (red in the original diagram) indicates the case of the compound of Reference Example 8; the grey vertical bar (blue in the original diagram) indicates the case of omeprazole (OMZ); the black upper thick mark (dark blue in the original diagram) indicates the case of lansoprazole (LAZ); and the grey upper thick mark (blue in the original diagram) indicates the case of rabeprazole (RAZ).

From the results of the present test, the compounds of Examples 1, 2 and 3, which were SH compounds, were all stable against acid, and all had residual ratios of 100% after 30 minutes and 2 hours. On the other hand, the SO-form compounds of Examples 1, 2 and 3 with the SH moieties oxidized, that is, the compounds of Reference Examples 6, 7 and 8, were all extremely unstable against acid, and all had residual ratios of 0% after 30 minutes and 2 hours. Furthermore, omeprazole, lansoprazole and rabeprazole, which are proton pump inhibitors widely used over the world at present, are all SO-form compounds, and the compounds were unstable against acid, and all had residual ratios of 0% after 30 minutes and 2 hours. From the above results, it was found that surprisingly, the SH-form compounds of the present invention were stable against acid.

Pharmacological Test Example 1

Antibacterial Potency Test

A test was conducted to see whether there is a difference in the anti-*Helicobacter pylori* activity depending on the number of carbon atoms of the linear alkyl group for a substituent at the 4-position of the pyridine ring.

(Method)

For the bacterium *Helicobacter pylori*, a standard strain ATCC 43504 was used to perform in vitro tests in Columbia agar medium. Each of the specimens was dissolved in a 1% DMSO solution, and the bacteria were cultured at 37° C. and pH 7.0 for 3 days. On the $4^{th}$ day, the minimum growth inhibitory concentration (MIC, µg/ml) was determined.

Figure 2:
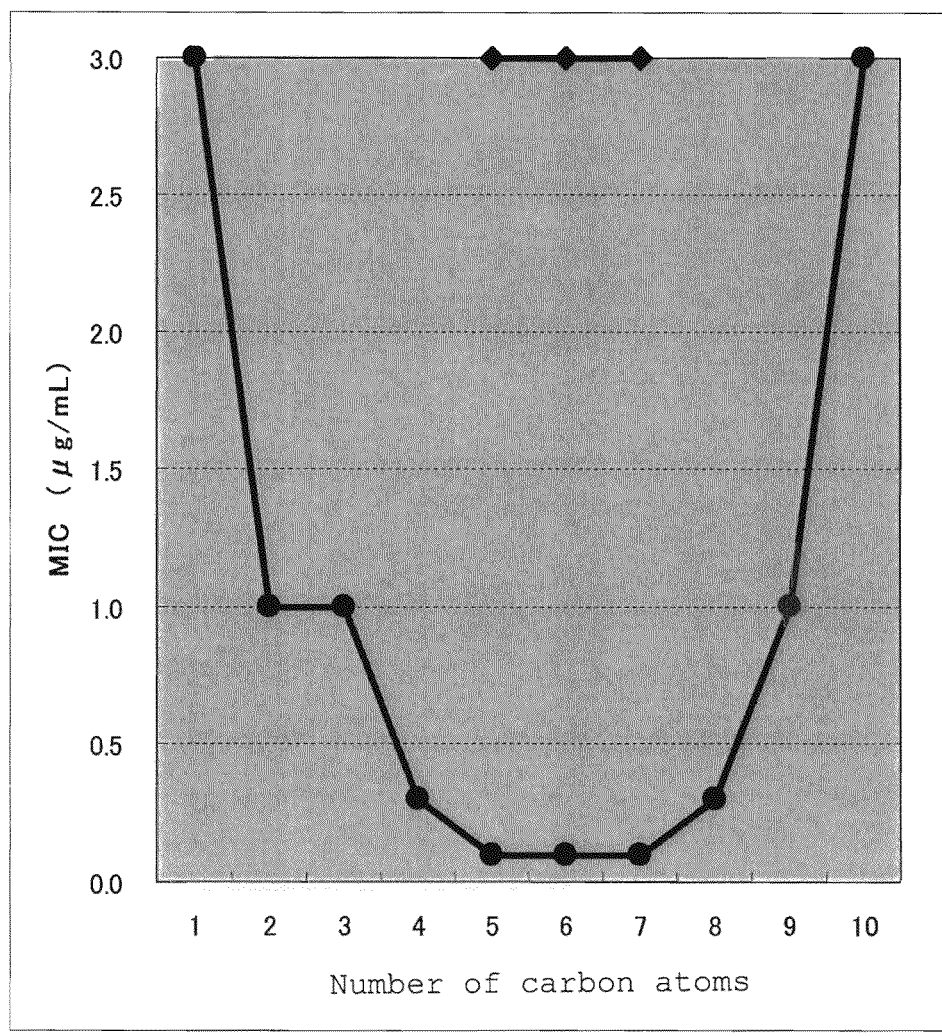
FIG. 2 is a graph showing the results of a test for the antibacterial activity (MIC) against *Helicobacter pylori* bacteria based on the presence or absence of oxidation of the thioether group of the compound of the present invention and of the compound of Comparative Example, and the difference in the number of carbon atoms of the alkyl group in the alkoxy group at the 4-position of pyridine. The vertical axis of FIG. 2 represents MIC (μg/mL), while the horizontal axis represents the number of carbon atoms of the alkyl group. The black circle mark in FIG. 2 (dark blue in the original diagram) indicates the case of SH-form, while the grey circle mark (red in the original diagram) indicates the case of SO-form.

The results are presented in Table 2 and FIG. 2.

TABLE 2

Number of carbon atoms and anti-Helicobacter pylori activity

| Number of carbon atoms of R | MIC (µg/mL) |
|---|---|
| 1 (Reference Example 1) | 3.0 |
| 2 (Reference Example 2) | 1.0 |
| 3 (Reference Example 3) | 1.0 |
| 4 (Example 4) | 0.3 |
| 5 (Example 1) | 0.1 |
| 6 (Example 2) | 0.1 |
| 7 (Example 3) | 0.1 |

TABLE 2-continued

Number of carbon atoms and anti-Helicobacter pylori activity

| Number of carbon atoms of R | MIC (µg/mL) |
|---|---|
| 8 (Example 5) | 0.3 |
| 9 (Reference Example 4) | 1.0 |
| 10 (Reference Example 5) | 3.0 |
| 5 (Reference Example 6) | 3.0 |
| 6 (Reference Example 7) | 3.0 |
| 7 (Reference Example 8) | 3.0 |

In FIG. 2, the vertical axis represents the MIC (µg/mL), while the horizontal axis represents the number of carbon atoms of the alkyl group. The black circle mark (dark blue in the original diagram) in FIG. 2 indicates the case of SH-form, and the grey circle mark (red in the original diagram) indicates the case of SO-form.

From the results of the present test, as it is obvious Table 2 and FIG. 2, it was found that with regard to the SH-form compounds, the anti-HP activity becomes specifically stronger when the number of carbon atoms of a particular linear chain is in the range of 2 to 9, and particularly in the range of 4 to 8. Further, the activity reached the maximum when the number of carbon atoms of the linear chain was 5, 6 or 7, exhibiting a value of 0.1 µg/ml. Furthermore, when the number of carbon atoms of the linear chain increased to 8 or 9, the anti-*Helicobacter pylori* action was attenuated, but even in that case, the MIC was 0.3 and 1.0 µg/mL, respectively, which values were respectively $\frac{1}{10}$ and $\frac{1}{3}$ as compared to the case of the number of carbon atoms being 1. On the other hand, the anti-HP activity of the SO-form compounds, which corresponded to Examples 1, 2 and 3 exhibiting this maximum anti-*Helicobacter pylori* activity, was all weak, exhibiting 3.0 µg/mL, regardless of the number of carbon atoms.

As such, it is the present invention to discover for the first time that the anti-*Helicobacter pylori* activity largely fluctuates with the number of carbon atoms of the linear alkyl group for a substituent at the 4-position of the pyridine ring, and it was also found that the fluctuation is maximized in the case where the number of carbon atoms of the linear chain is 5, 6 or 7, and thus the fluctuation does not depend on the number of carbon atoms in a simple manner. The maximum value is even about 30 times the value of the case where the number of carbon atoms is 1 or 10. Furthermore, it could be also confirmed that there is obtained a surprising result that the activity is stronger by about 30 times, even in comparison to the corresponding SO-form compounds.

Pharmacological Test Example 2

Method

For the bacterium *Helicobacter pylori*, standard strains ATCC 43504, ATCC 43629 and ATCC 43570 were used to perform in vitro tests in Columbia agar medium. The bacteria were cultured at 37° C. and pH 7.0 for 3 days. On the $4^{th}$ day, the minimum growth inhibitory concentration (MIC, µg/ml) was determined. Each of the specimens was dissolved in a 1% DMSO solution. Furthermore, amoxicillin and clarithromycin were used as control drugs of antibacterial substance. Further, the compound described in the article of Thomas C. Kuehler (J. Med. Chem. 1998, 41, 1777-1788) (Comparative Example 1) and the compound described in the Patent Document 2 (Comparative Example 2) were synthesized and used for comparison.

The results are presented in Table 3 (Anti-*Helicobacter pylori* activity of thioether derivatives (MIC: µg/ml)).

TABLE 3

Anti-*Helicobacter pylori* activity of thioether derivatives (MIC: μg/ml)

|  | Strain | Example 1 | Example 2 | Example 3 | Comparative Example 1 | Comparative Example 2 | Control Drug AMPC | Control Drug CAM |
|---|---|---|---|---|---|---|---|---|
| Standard strain | ATCC 43504 | 0.1 | 0.1 | 0.1 | 3 | 10 | 0.06 | 0.1 |
|  | ATCC 43629 | 0.06 | 0.1 | 0.1 | 1 | 10 | 0.06 | 0.1 |
|  | ATCC 43570 | <0.015 | 0.03 | 0.1 | 1 | 5 | <0.015 | <0.015 |
| Clinically Separated strain | PT1045 482 | 0.1 | 0.1 | 0.1 | 3 | 10 | 0.06 | 0.3 |
|  | PT1045 483 | 0.06 | 0.1 | 0.1 | 3 | 10 | 0.06 | 0.3 |
|  | PT1045 484 | 0.06 | 0.1 | 0.1 | 1 | 10 | 0.06 | 0.3 |

In the Table 3, AMPC indicates amoxicillin, and CAM indicates clarithromycin. Further, the compound of Comparative Example 1 is 2-[(4-isobutoxy-3-methylpyridin-2-yl)methylthio]-1H-benzimidazole, and the compound of Comparative Example 2 is 2-[(4-isobutoxy-pyridin-2-yl)methylthio]-1H-benzimidazole.

From the results of the present test, it was recognized that the compounds of Examples 1, 2 and 3 had strong antibacterial activity against the respective standard strains and clinically separated strains of the bacterium *Helicobacter pylori*. It was also made clear that the compounds of Examples had an obviously strong anti-*Helicobacter pylori* bacteria activity as compared with the Comparative Examples, and showed an anti-*Helicobacter pylori* bacteria activity that is equivalent to that of antibacterial agent amoxicillin or clarithromycin.

Pharmacological Test Example 3

A test was conducted on the antibacterial potency of the compounds of the present invention against the clarithromycin-resistant strains and amoxicillin-insensitive strains of the bacterium *Helicobacter pylori*.

(Method)

A test was conducted on the antibacterial potency of the compounds of the present invention, using clinically separated clarithromycin-resistant strains and amoxicillin-insensitive strains of the bacterium *Helicobacter pylori*. For the respective strains, in vitro tests were performed in Columbia agar medium. Each of the specimens was dissolved in a 1% DMSO solution. The bacteria were cultured at 37° C. and pH 7.0 for 3 days, and on the 4$^{th}$ day, the minimum growth inhibitory concentration (MIC, μg/ml) was determined.

The results are presented in the following Table 4 (Effects of thioether derivatives on resistant *Helicobacter pylori* bacteria (MIC: μg/ml)).

TABLE 4

Effects of thioether derivatives on resistant *Helicobacter pylori* bacteria (MIC: μg/ml)

|  | NO. | Example 1 | Example 2 | Example 3 | CAM | AMPC |
|---|---|---|---|---|---|---|
| CAM-resistant strain | 1 | 0.06 | 0.06 | 0.1 | 32 | <0.015 |
|  | 2 | 0.06 | 0.06 | 0.1 | 8 | <0.015 |
|  | 3 | 0.06 | 0.06 | 0.1 | 64 | <0.015 |
|  | 4 | 0.06 | 0.06 | 0.1 | 32 | <0.015 |
| AMO-Insensitive | 1 | 0.06 | 0.06 | 0.12 | 0.06 | 0.25 |
|  | 2 | 0.06 | 0.12 | 0.12 | 0.03 | 0.25 |

TABLE 4-continued

Effects of thioether derivatives on resistant *Helicobacter pylori* bacteria (MIC: μg/ml)

|  | NO. | Example 1 | Example 2 | Example 3 | CAM | AMPC |
|---|---|---|---|---|---|---|
| strain | 3 | 0.06 | 0.12 | 0.12 | 0.06 | 0.25 |
|  | 4 | 0.06 | 0.12 | 0.25 | 0.03 | 0.12 |

CAM: Clarithromycin
AMPC: Amoxicillin

In the Table 4, CAM indicates clarithromycin, and AMPC indicates amoxicillin.

From the results shown above, the compounds of Examples 1, 2 and 3 exhibited strong antibacterial activity against the clarithromycin-resistant strains and the amoxicillin-insensitive strains. Since amoxicillin and clarithromycin are widely used at present as a therapy for eradication of *Helicobacter pylori* bacteria, and in particular, clarithromycin-resistant strains are increasing, it could be seen that the present invention is also effective against resistant bacteria, and the clinical usefulness is also very high.

Pharmacological Test Example 4

An antibacterial test against Gram-negative bacteria and Gram-positive bacteria was conducted with the compounds of the present invention.

(Method)

As for the Gram-negative bacteria, *E. coli* (ATCC 10536, ATCC 25922), *Klebsiella pneumonia* (ATCC 10031), *Proteus vulgaris* (ATCC 13315), *Pseudomonas aeruginosa* (ATCC 9027), and *Salmonella typhimurium* (ATCC 13311) were used, and as for the Gram-positive bacteria, *Staphylococcus aureus*, MRSA (ATCC 33591), *Staphylococcus epidermidis* (ATCC 12228), *Streptococcus pneumonia* (ATCC 6301), *Mycobacterium ranae* (ATCC 110), and *Enterococcus faecalis* (VRE, ATCC 51575) were used. The various bacteria were cultured at 37° C. for 20 to 48 hours by conventional methods, and the minimum growth inhibitory concentration (MIC, μg/ml) was determined. Each of the specimens was dissolved in a 1% DMSO solution. Furthermore, amoxicillin, clarithromycin and gentamycin were used as control drugs of antibacterial substance.

The results are presented in Table 5 (Effects of thioether derivatives on Gram-negative bacteria and Gram-positive bacteria (MIC: μg/ml)).

TABLE 5

Effects of thioether derivatives on Gram-negative bacteria and Gram-positive bacteria (MIC: μg/ml)

| | Bacterial species | Example 1 | Example 2 | Example 3 | AMPC | CAM | GEM |
|---|---|---|---|---|---|---|---|
| Gram-Negative bacteria | Escherichia coli (ATCC 10536) | >100 | >100 | >100 | 6.25 | 50 | 0.3 |
| | Escherichia coli (ATCC 25922) | >100 | >100 | >100 | 6.25 | 50 | 1.0 |
| | Klebsiella pneumonia (ATCC 10031) | >100 | >100 | >100 | — | — | 1.0 |
| | Proteus vulgaris (ATCC 13315) | >100 | >100 | >100 | 6.25 | 100 | 0.3 |
| | Pseudomonas aeruginosa (ATCC 9027) | >100 | >100 | >100 | 100< | 100< | 0.3 |
| | Salmonella typhimurium (ATCC 13311) | >100 | >100 | >100 | 0.3 | 25 | 1.0 |
| Gram-Positive bacteria | Staphylococcus aureus, MRSA (ATCC 33591) | >100 | >100 | >100 | 0.1 | 0.1 | 1.0 |
| | Staphylococcus epidermidis (ATCC 12228) | >100 | >100 | >100 | — | — | 0.1 |
| | Streptococcus pneumonia (ATCC 6301) | >100 | >100 | >100 | 0.01 | 0.02 | — |
| | Mycobacterium ranae (ATCC 110) | >100 | >100 | >100 | — | — | 0.3 |
| | Enterococcus faecalis (VRE, ATCC 51575) | >100 | >100 | >100 | 0.3 | 0.1 | — |

AMPC: Amoxicillin
CAM: Clarithromycin
GEM: Gentamycin

In the Table 5, AMPC indicates amoxicillin, CAM indicates clarithromycin, and GEM indicates gentamycin.

From the results of this test, the compounds of the present invention were all not recognized to have antibacterial action against various Gram-negative bacteria and Gram-positive bacteria. On the other hand, amoxicillin, clarithromycin and gentamycin exhibited strong antibacterial action against various Gram-negative bacteria and Gram-positive bacteria. From these matters, it was shown that the compounds of the present invention do not exert influence on intestinal bacteria.

Pharmacological Test Example 5

Mongolian gerbils were experimentally infected with *Helicobacter pylori* bacteria, and the antiulcer action and the *Helicobacter pylori* bacteria eradicating action of the compounds of the present invention were tested.

(Method)

Male Mongolian gerbils (30 to 40 g), five animals in each group, were orally inoculated with *Helicobacter pylori* bacteria (ATCC 43504) at $1.6 \times 10^7$ CFU/0.5 ml/mouse, and bred for one week, and then drug was administered two times a day for two weeks. Thereafter, the rats were bred for three weeks, and then the rats were fasted for 18 hours and subjected to abdominal section, followed by autopsy. The severity of gastric ulcer, the number of *Helicobacter pylori* bacteria in the gastric mucosa, and the antibody titer were measured.

The results are presented in Table 6 (Antiulcer action and bacteria eradicating action in *H. pylori*-infected mice).

TABLE 6

Antiulcer action and bacteria eradicating action in *H. pylori*-infected mice

| | Number of Ulcers discovered | Eradication rate (%) | Number of Bacteria (average) (log CFU) | Antibody titer (average) |
|---|---|---|---|---|
| Control group (0.5% CMC) | 5/5 | 0 | 5.6 | 0.43 |
| Example 1 30 mg/kg | 0/5 | 100 | <3 | 0.05 |
| Example 1 10 mg/kg | 0/5 | 100 | <3 | 0.07 |
| Example 2 30 mg/kg | 0/5 | 100 | <3 | 0.17 |
| Example 3 30 mg/kg | 0/5 | 100 | <3 | 0.22 |
| Comparative Example 1 30 mg/kg | 5/5 | 0 | 6.3 | 0.49 |
| Comparative Example 2 30 mg/kg | 5/5 | 0 | 5.9 | 0.55 |
| Omeprazole (OMZ) 10 mg/kg | 5/5 | 0 | 6.0 | 0.52 |
| Clarithromycin (CAM) 30 mg/kg | 4/5 | 20 | 5.2 | 0.35 |
| Amoxicillin (AMPC) 10 mg/kg | 4/5 | 20 | 5.0 | 0.40 |
| OMZ + CAM + AMPC | 0/5 | 100 | <3 | 0.08 |

Comparative Example 1: 2-[(4-isobutoxy-3-methylpyridin-2-yl)methylthio]-1H-benzimidazole
Comparative Example 2: 2-[(4-isobutoxy-pyridin-2-yl)methylthio]-1H-benzimidazole In the Table 6, the compound of Comparative Example 1 is 2-[(4-isobutoxy-3-methylpyridin-2-yl)methylthio]-1H-benzimidazole, and the compound of Comparative Example 2 is 2-[(4-isobutoxy-pyridin-2-yl)methylthio]-1H-benzimidazole. Further, OMZ indicates omeprazole, CAM indicates clarithromycin, and AMPC indicates amoxicillin.

As it is obvious from the results described above, omeprazole, which is a gastric acid secretion inhibitor, clarithromycin and amoxicillin, which are antibacterial agents, and the compounds of the Comparative Examples were not recognized to have an antiulcer action and a bacteria eradicating action in the *Helicobacter pylori* bacteria-infected model when used singly. On the other hand, the triple combination (omeprazole, clarithromycin and amoxicillin), which is an active control, was clearly recognized to have an antiulcer action and a *Helicobacter pylori* bacteria eradicating action. From this, it could be seen that the compounds of the present invention have an effectiveness comparable to the triple combination therapy that is widely practiced clinically at present as a *Helicobacter pylori* bacteria eradicating therapy, even when used singly.

From the results of the present experiment, the compounds of the present invention exhibited an antiulcer action and a *Helicobacter pylori* bacteria eradicating action which were similar to those of the active control, when used singly. In particular, the compound of Example 1 inhibited generation of ulcer even at a low amount of administration of 10 mg/kg, and exhibited a strong *Helicobacter pylori* bacteria eradicating action. From this, it was strongly indicated that the subject agent is clinically very useful as a *Helicobacter pylori* bacteria eradicating agent.

Pharmacological Test Example 6

The gastric acid secretion inhibiting action of the compounds of the present invention was tested.

(Method)

A group of five animals of male SD rats (about 200 g) were used, and the medicaments were respectively dissolved in 0.5% CMC and were all administered to the duodenum respectively at 30 mg/kg. The rats were fasted overnight from the day before the administration of the test substance to the point of administration, and pylorus ligation was performed. After 4 hours, the stomach was extracted under ether anesthesia, and the amount of gastric juice and the total acidity were measured according to standard methods.

The results are presented in Table 7 (Gastric acid secretion inhibiting action of novel pyridine derivatives (average %)).

TABLE 7

Gastric acid secretion inhibiting action of novel pyridine derivatives (average %)

|  | Example 1 | Example 2 | Example 3 | Control drug |
|---|---|---|---|---|
| Amount of gastric acid | 57 | 44 | 44 | 54 |
| Total acidity | 60 | 34 | 44 | 41 |
| Amount of gastric acid secretion | 82 | 65 | 70 | 74 |

Control drug: Cimetidine

The control drug in the Table 7 is cimetidine.

From the above results, the compounds of the present invention all exhibited a gastric acid secretion inhibiting effect, and the potency was almost equal to that of cimetidine.

A summary of the results of the above-described stability test and Pharmacological Test Examples is presented in the following Table 8 (Summary).

[Table 8]

TABLE 8

Summary

| n | Number of carbon atoms of R | Stability in acid (residual ratio at pH = 2: %) | Anti-HP activity (MIC: μg/mL) | HP eradication based on Mongolian gerbil infection model | |
|---|---|---|---|---|---|
| | | | | Amount of administration (mg) | Eradication rate (%) |
| 0 (—S—) | 5 (Example 1) | 100 | 0.1 | 10 | 100 |
| | 6 (Example 2) | 100 | 0.1 | 30 | 100 |
| | 7 (Example 3) | 100 | 0.1 | 30 | 100 |
| 1 (S=O) | 5 (Reference Example 6) (oxide of Example 1) | 0 | 3.0 | 30 | 0 |
| | 6 (Reference Example 7) (oxide of Example 2) | 0 | 3.0 | 30 | 0 |
| | 7 (Reference Example 8) (oxide of Example 3) | 0 | 3.0 | 30 | 0 |
| PPI | OMZ | 0 | 128 | 30 | 0 |
| | LAZ | 0 | 16 | 30 | 0 |
| | RAZ | 0 | 8 | 30 | 0 |
| Triple | OME + AMPC + CAM | — | — | 10 + 10 + 30 | 100 |

OMZ: Omeprazole,
LAZ: Lansoprazole,
RAZ: Rabeprazole,
AMPC: Amoxicillin,
CAM: Clarithromycin In the Table 8, OMZ indicates omeprazole, LAZ indicates lansoprazole, RAZ indicates rabeprazole, AMPC indicates amoxicillin, and CAM indicates clarithromycin.

As discussed in the above, it was found that while SO-forms (sulfoxide form compounds) are very unstable in acid, SH-forms (thioether form compounds) are stable in acid, and that when the number of carbon atoms of linear chain for R is 5, 6 or 7, a specifically very strong anti-*Helicobacter pylori* bacteria activity is exhibited. Furthermore, these three kinds of compounds exhibited a *Helicobacter pylori* bacteria eradicating action when used as a sole agent, also in an in vivo infection model utilizing Mongolian gerbil. The potency of the action was equal to or greater than the triple combination of omeprazole+amoxicillin+clarithromycin, which is widely practiced over the world as a therapy for *Helicobacter pylori* bacteria eradication. Furthermore, it was confirmed that the compounds of the present invention exhibit a specific antibacterial activity against *Helicobacter pylori* bacteria, exhibit an antibacterial action even against the bacteria that are insensitive or resistant to amoxicillin and clarithromycin, and have a gastric acid secretion inhibiting action.

Preparation Examples using the compound of the present invention will be described in the following.

Preparation Example 1

Tablet Preparation

| | |
|---|---|
| Compound 1 (compound produced in Example 1) | 50.0 mg |
| Mannitol | 20.3 mg |
| Hydroxypropyl cellulose | 2.5 mg |
| Crystalline cellulose | 10.0 mg |
| Cornstarch | 10.0 mg |
| Carboxymethyl cellulose calcium | 5.0 mg |
| Talc | 2.0 mg |
| Magnesium stearate | 0.2 mg |

A tablet preparation weighing 100 mg per tablet was prepared at the above-described blending ratio, according to a routine method.

Preparation Example 2

Granule Preparation

| | |
|---|---|
| Compound 2 (compound produced in Example 2) | 300 mg |
| Lactose | 540 mg |
| Maize starch | 100 mg |
| Hydroxypropyl cellulose | 50 mg |
| Talc | 10 mg |

A granule preparation weighing 1000 mg per pouch was prepared at the above-described blending ratio, according to a routine method.

Preparation Example 3

Capsule Preparation

| | |
|---|---|
| Compound 1 | 50 mg |
| Lactose | 15 mg |
| Maize starch | 25 mg |
| Microcrystalline cellulose | 5 mg |
| Magnesium stearate | 1.5 mg |

A capsule preparation weighing 96.5 mg per capsule was prepared at the above-described blending ratio, according to a routine method.

Preparation Example 4

Injectable Preparation

| | |
|---|---|
| Compound 1 | 100 mg |
| Sodium chloride | 3.5 mg |
| Distilled water for injection (2 ml per ampoule) | Adequate amount |

An injectable preparation was prepared at the above-described blending ratio, according to a routine method.

Preparation Example 5

Syrup Preparation

| | |
|---|---|
| Compound 1 | 200 mg |
| Purified sucrose | 6.0 g |
| Ethyl parahydroxybenzoate | 5 mg |
| Butyl parahydroxybenzoate | 5 mg |
| Fragrance | Adequate amount |
| Coloring matter | Adequate amount |
| Purified water | Adequate amount |

A syrup preparation was prepared at the above-described blending ratio, according to a routine method.

Preparation Example 6

Tablet Preparation

| | |
|---|---|
| Compound 1 | 50 mg |
| Famotidine | 20 mg |
| Cyclodextrin | 26 mg |
| Microcrystalline cellulose | 5 mg |
| Hydroxypropyl cellulose | 5 mg |
| Talc | 2 mg |
| Magnesium stearate | 2 mg |

A tablet preparation weighing 120 mg per tablet was prepared at the above-described blending ratio, according to a routine method.

INDUSTRIAL APPLICABILITY

The present invention is to provide a compound which is stable against acid, has an antibacterial action against *Helicobacter pylori* bacteria, exhibits a sufficient antibacterial action when used as a sole agent, does not affect intestinal bacteria, has an antibacterial action even on the bacteria resistant to antibacterial agents, and has a gastric acid secretion inhibiting action, and a pharmaceutical composition making use of the compound, and the invention is useful for the pharmaceutical industry and the like, while having an industrial applicability.

The invention claimed is:

1. A pyridine derivative represented by formula (I), or a pharmaceutically acceptable salt thereof:

[Chemical Formula 5]

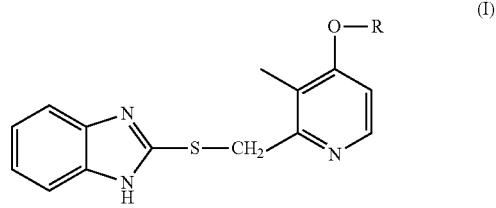

(I)

wherein R represents a linear alkyl group having 4 to 8 carbon atoms.

2. The pyridine derivative or the salt according to claim 1, wherein R in the formula (I) is a linear alkyl group having 5 to 7 carbon atoms.

3. A pharmaceutical composition comprising the pyridine derivative according to claim 1 or a pharmaceutically acceptable salt thereof, and a pharmaceutically acceptable carrier.

* * * * *